(12) United States Patent
Spring et al.

(10) Patent No.: US 7,256,008 B2
(45) Date of Patent: Aug. 14, 2007

(54) DETERMINATION OF CONCENTRATION OF FK778 BY COMPETITIVE IMMUNOASSAY

(75) Inventors: Thomas G. Spring, Highland Park, IL (US); Elaine M. Brate, Grayslake, IL (US); Shelley Holets-McCormack, Waukegan, IL (US); Rajarathnam E. Reddy, Gurnee, IL (US); Donald D. Johnson, Lindenhurst, IL (US); Yon-Yih Chen, Mundelein, IL (US); You Pan, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/327,711

(22) Filed: Jan. 6, 2006

(65) Prior Publication Data

US 2007/0161123 A1    Jul. 12, 2007

(51) Int. Cl.
    *G01N 33/00*     (2006.01)
(52) U.S. Cl. ..................... 435/7.93; 435/7.1; 435/7.92; 436/518; 436/524
(58) Field of Classification Search ................. 435/7.1, 435/7.92–7.95, 968; 436/501, 518, 524, 436/164, 172
See application file for complete search history.

(56) References Cited

U.S. PATENT DOCUMENTS

| | | | |
|---|---|---|---|
| 5,294,404 A | 3/1994 | Grandone et al. | |
| 5,795,784 A | 8/1998 | Arnquist et al. | |
| 5,856,194 A | 1/1999 | Arnquist et al. | |
| 6,893,875 B2 * | 5/2005 | Tsuji et al. | ................ 436/172 |

FOREIGN PATENT DOCUMENTS

| | | | |
|---|---|---|---|
| GB | EP 0177191 | * | 9/1986 |
| WO | WO 98/00696 | | 7/1998 |

(Continued)

OTHER PUBLICATIONS

Bilolo, K.K., et al., "Synergistic Effects of Malononitrilamides (FK778, FK779) With Tacrolimus (FK506) in Prevention of Acute Heart and Kidney Allograft Rejection and Reversal of Ongoing Heart Allograft Rejection in the Rat", *Transplantation*, 75(11):1881-1887 (2003).

(Continued)

*Primary Examiner*—Long V. Le
*Assistant Examiner*—Gary W. Counts
(74) *Attorney, Agent, or Firm*—David L. Weinstein

(57) ABSTRACT

Methods and kits for measurement of concentration of FK778 in a biological sample by means of an immunoassay, preferably a competitive immunoassay. In one aspect, the method and kit involve the use of (a) an antibody to FK778 conjugated to a label, e.g., an acridinium label, (b) an antibody to FK778 not conjugated to a label, (c) a solid phase containing an antibody to a first hapten, e.g., a fluorescein hapten, and (d) a bihapten comprising a first hapten and FK778 or an analogue of FK778, e.g., a bihapten comprising a fluorescein hapten and a FK778 hapten. In another aspect, the method and kit involve the use of (a) antibody to FK778, (b) a bihapten comprising FK778 or an analogue of FK778 and a first hapten, e.g., a bihapten comprising the fluorescein hapten and the hapten of FK778 or an analogue of FK778, and (c) a pretreatment reagent.

3 Claims, 5 Drawing Sheets

FOREIGN PATENT DOCUMENTS

WO       2005/085290 A1 *  9/2005
WO   WO 2005/085290 A1     9/2005

OTHER PUBLICATIONS

Birsan, T., et al., "Effects of the malononitrilamide FK778 on immune functions in vitro in whole blood from non-human primates and healthy human volunteers", *Transplant Immunology*, 11:163-167 (2003).

Birsan, T., et al., "In vivo pharmacokinetic and pharmacodynamic evaluation of the malononitrilamide FK778 in non-human primates", *Transpl. Int.*, 16:354-360 (2003).

Evers, D.L., et al., "Inhibition of human cytomegalovirus signaling and replication by the immunosuppressant FK778", *Antiviral Research*, xxx (2004) xxx-xxx.

Fawcett, J. et al., "FK778: A Powerful Immunosuppressive, But Will It really be Good for You?", *Transplantation*, 78(1):7-8 (2004).

First, M.R., et al., "New Drugs to Improve Transplant Outcomes", *Transplantation*, 77(9):S88-S92 (2004).

Jin, M.B., et al., "A novel leflunomide derivative, FK778, for ummunosuppression after kidney transplantation in dogs", *Surgery*, 132(1):72-79 (2002).

Savikko, J., et al., "Leflunomide Analogue FK778 is Vasculoprotective Independent of its Immunosuppressive Effect: Potential Applications for Restenosis and Chronic Rejection", *Transplantation*, 76(3):455-458 (2003).

Savikko, J., et al., "Leflunomide Analogue FK778 Is Vasculoprotective Independent of its Immunosuppressive Effect: Potential Application for Restenosis and Chronic Rejection", *Transplantation*, 76(3):471-473 (2003).

Slauson, S.D., et al., "Flow cytometric analysis of the molecular mechanisms of immunosuppressive action of the active metabolite of leflunomide and its malononitrilamide analogues in a novel whoe blood assay", *Immunology Letters.*, 67:179-183 (1999).

Taylor, P.J., "Therapeutic Drug Monitoring of Immunosuppressant Drugs by High-Performance Liquid Chromatography-Mass Spectrometry", *Ther. Drug Monit.*, 26(2):215-219 (2004).

Vanrenterghem, Y., et al., "The Effects of FK778 in Combination With Racrolimus and Steroids: A Phase II Multicenter Study in Renal Transplant Patients", *Transplantation*, 78(1):9-14 (2004).

Adamczyk, et al., A Stereoselective Synthesis of 1α-(3'-Carboxypropyl)-4-androsten-17β-ol-3-one: Preperation of Immunoreagents for Quantification of Testosterone by Fluorescence Polarization Immunoassay, *Tetrahedron*, vol. 53, No. 38, 12855-12866 (1997).

PCT Search Report.

* cited by examiner

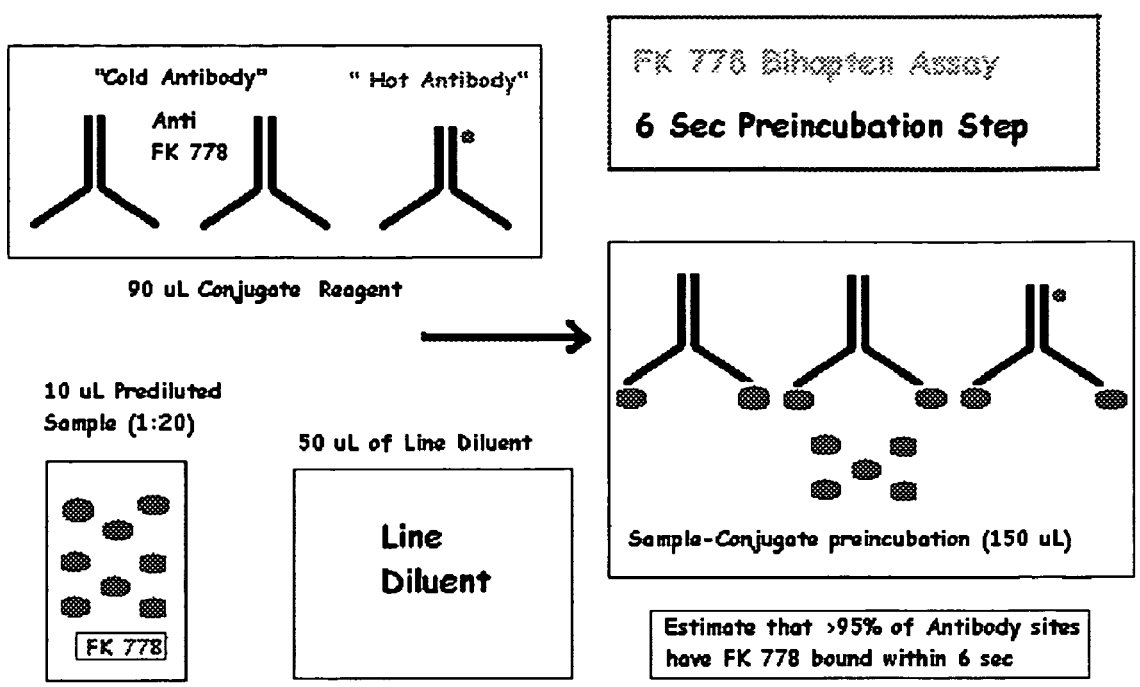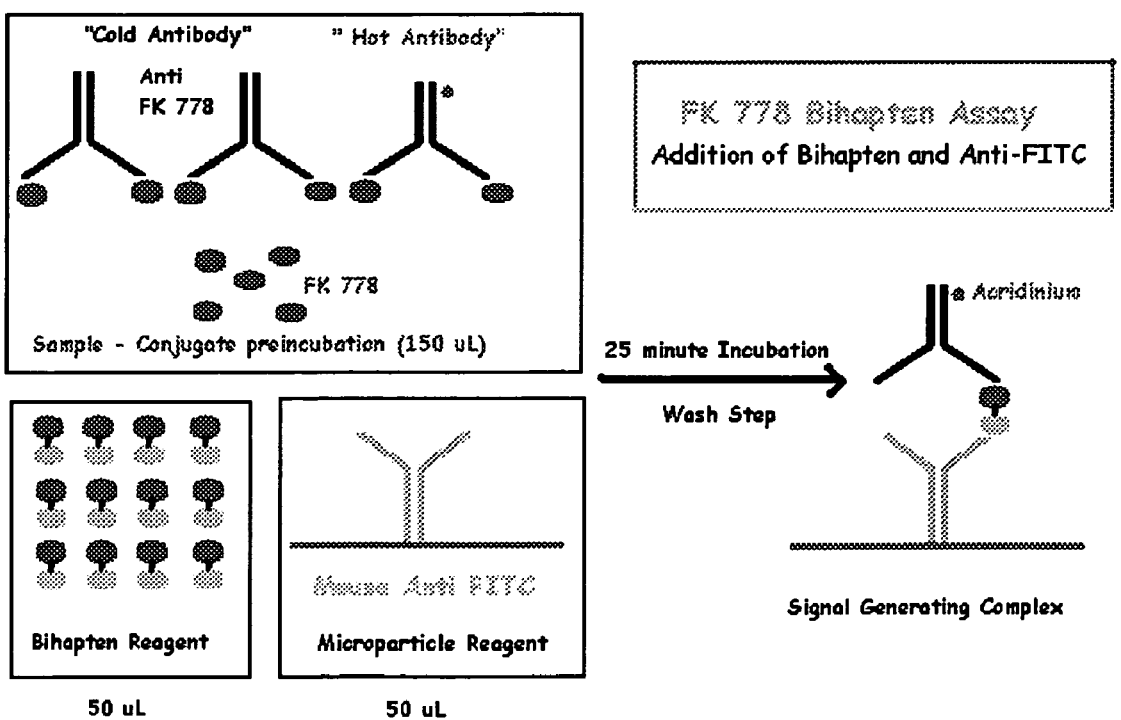
FIG. 1

Antibody Conjugation Process
Process Step

| |
|---|
| Concentrate Anti FK778 to > 7.2 mg/mL, if needed<br>Prepare 4 mg/mL CPSP active ester in DMF<br>Prepare Conjugation Buffer |

⇓

| |
|---|
| Prepare 3 mL reaction mixture containing:<br>20 mg Antibody + 200 microliters Conjugation Buffer<br>24 μg CPSP active ester ( 6 microliters of 4 mg/mL)<br>PBS to make final volume to 3 mL |

⇓

| |
|---|
| React for 20 minutes at Room Temperature<br>Transfer to a Slide-a-lyzer dialysis device<br>Dialyse at 4 deg. C > 24 hours vs. 250 mL Dialysis buffer |

⇓

| |
|---|
| Filter dialysed reaction mixture through 0.2 micron filter<br>Measure 370 nm absorbance in a 1 cm cuvette<br>Measure 280 nm absorbance in 0.1 cm cuvette |

⇓

| |
|---|
| Calculate Acridinium Incorporation Ratio (target 0.25)<br>Size exclusion HPLC to measure aggregates, free CPSP<br>Dilute conjugate to 300 μg/mL in Conjugate diluent (1000X) |

FIG. 4

DETERMINATION OF CONCENTRATION OF FK778 BY COMPETITIVE IMMUNOASSAY

BACKGROUND OF THE INVENTION

1. Field of the Invention

This invention relates to detection and measurement of FK778 or analogues of FK778 in biological samples, and, more particularly, detection and measurement of FK778 or analogues of FK778 in biological samples by means of competitive immunoassay.

2. Discussion of the Art

FK778 (previously known as HMR 1715, X92 0715, or MNA 715) is structurally similar to A77 1726, the active metabolite of leflunomide. Like A77 1726, FK778 is a malononitrilamide; these compounds are effective immunosuppressants in experimental models of autoimmune diseases and in allo- or xeno-transplantation. While leflunomide (Arava™) has been released for clinical use in rheumatoid arthritis, the long plasma half-life of A77 1726 in humans (15-18 days) makes the drug undesirable for use in clinical transplantation. FK778 has a shorter plasma half-life in humans and thus holds promise that it might be useful in clinical transplantation. The structures of FK778 and A77 1726 are set forth below.

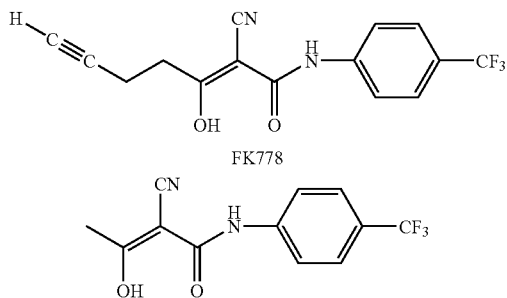

Lefluonomide Metabolite A77 1726

FK778 is described in greater detail in the following articles, all of which are incorporated herein by reference:

Bilolo et al., "SYNERGISTIC EFFECTS OF MALONONITRILIAMIDES (FK778, FK779) WITH TACROLIMUS (FK506) IN PREVENTION OF ACUTE HEART AND KIDNEY ALLOGRAFT REJECTION AND REVERSAL OF ONGOING HEART ALLOGRAFT REJECTION IN THE RAT", Transplantation, Vol. 75, 1881-1887, No. 11, Jun. 15, 2003.

Birsan et al., "In vivo pharmacokinetic and pharmacodynamic evaluation of malononitrilamide FK778 in non-human primates", Transpl. Int. (2003) 16: 354-360.

Birsan et al., "Effects of the malononitrilamide FK778 on immune functions in vitro in whole blood from non-human primates and healthy human volunteers", Transplant Immunology 11 (2003) 163-167.

Fawcett et al., "FK778: A Powerful Immunosuppressive, But Will It Really Be Good for You?", Transplantation, Volume 78, Number 1, Jul. 15, 2004.

Evers et al., "Inhibition of human cytomegalovirus signaling and replication by the immunosuppressant FK778", Antiviral Research xxx (2004) xxx-xxx.

First et al., "NEW DRUGS TO IMPROVE TRANSPLANT OUTCOMES", Transplantation, Vol. 77, S88-S92, No. 9, May 15, 2004 Supplement.

Jin et al., "A novel leflunomide derivative, FK778, for immunosuppression after kidney transplantation in dogs", Surgery, Volume 132, Number 1, 72-79, July 2002.

Savikko et al., "Leflunomide Analogue FK778 Is Vasculoprotective independent of its Immunosuppressive effect: Potential Application for Restenosis and Chronic Rejection", Transplantation 2003; 76: 455, Transplantation, Vol. 76, 471-473, No. 3, Aug. 15, 2003.

Savikko et al., "LEFLUNOMIDE ANALOGUE FK778 IS VASCULOPROTECTIVE INDEPENDENT OF ITS IMMUNOSUPPRESSIVE EFFECT: POTENTIAL APPLICATIONS FOR RESTENOSIS AND CHRONIC REJECTION", Transplantation, Vol. 76, 455-458, No. 3, Aug. 15, 2003.

Slauson et al., "Flow cytometric analysis of the molecular mechanisms of immunosuppressive action of the active metabolite of leflunomide and its malononitrilamide analogues in a novel whole blood assay", Immunology letters 67 (1999) 179-183.

Vanrenterghem et al., "The Effects of FK778 in Combination With Tacrolimus and Steroids: A Phase II Multicenter Study in Renal Transplant Patients", Transplantation, Volume 78, Number 1, Jul. 15, 2004.

Detection and measurement of FK778 in biological samples is important for monitoring therapeutic drugs, as an aid in adjusting drug dosage. The concentration of drug in plasma correlates to the degree of immunosuppression.

FK778 can be determined by LC/Tandem Mass Spectrometry. Methods for LC/Tandem Mass Spectrometry are described in the following reference, which is incorporated herein by reference:

Therapeutic Drug Monitoring of Immunosuppressant Drugs by High-performance Liquid Chromatography-Mass Spectrometry. Taylor, Paul J. Therapeutic Drug Monitoring 26(2):215-219, April 2004

Determination of the presence and amount of FK778 or analogues of FK778 in a biological sample can be determined by a competitive diagnostic assay. Small molecule, competitive diagnostic assays usually require a labeled component that can compete with the analyte for available antibody sites. The labeled component is typically referred to as a tracer. Examples of the labeled component include radioactive tracers, fluorescent tracers, chemiluminescent tracers, and enzyme tracers. Typically, the labeled component consists of the analyte or an analogue of the analyte coupled to a label.

The probability that a particular reagent comprising an antibody to FK778 and a labeled component will be useful in a sensitive assay for FK778 can be assessed by knowledge of the dose response curve. The dose response curve for a FK778 assay is a plot of the ratio of the response in the presence of FK778 analyte to the response in the absence of FK778 analyte as a function of the concentration of the FK778 analyte. The dose response curve for a given FK778 assay is unique for each reagent comprising an antibody to FK778 and a tracer and is modulated by the competition between the tracer and the analyte for sites on the antibody to the analyte.

The problem with a typical FK778 competitive immunoassay on an automated chemiluminescent analyzer is that the tracer comprising FK778 and an acridinium label has a very potent signal. Consequently, the tracer must be diluted to a very low concentration to be measured by the analyzer. FK778 analyte is present at a very high concentration in biological samples. Accordingly, the sample must be diluted more than 1000-fold to compete effectively with the tracer. This degree of sample dilution is typically not available on an automated analyzer. Failure to provide such a dilution results in an assay in which the concentration of FK778 exceeds the concentration of the tracer by so much that the dose response curve is too steep in the dynamic range for a reliable assay. It is desired to develop a competitive assay that allows effective competition between a tracer and the analyte but contains a labeled component that is not as potent as the tracer comprising FK778 and an acridinium label. It would be desirable to provide a competitive immunoassay format capable of detecting levels of FK778 above 10 μg/mL and below 250 μg/mL, concentrations that are clinically useful but difficult to measure.

The company that developed the FK778 drug for clinical use (formerly Fujisawa, now Astellas) also developed and evaluated a series of monoclonal antibodies to FK778 using an ELISA procedure. It was required that these antibodies have sufficient affinity for FK778 in order to be used in an immunoassay. In addition, even when antibodies that demonstrated an appropriate affinity for the FK778 analyte were developed, many of these antibodies demonstrated the undesirable property of high cross-reactivity to structurally similar analogues of FK778, such as metabolites. These antibodies were further screened by Fujisawa for degree of cross-reactivity to metabolites and an antibody having low cross-reactivity was selected.

SUMMARY OF THE INVENTION

This invention provides methods and kits for measurement of concentration of FK778 in a biological sample by means of an immunoassay, preferably a competitive immunoassay.

In one aspect, the method and kit involve the use of (a) an antibody to FK778 conjugated to a label, e.g., an acridinium label, (b) an antibody to FK778 not conjugated to a label, (c) a solid phase containing an antibody to a first hapten, e.g., a fluorescein hapten, and (d) a bihapten comprising a first hapten and FK778 or an analogue of FK778, e.g., a bihapten comprising a fluorescein hapten and a FK778 hapten. The bihapten (d) provides a bridge between (a) the antibody to FK778 conjugated to a label and (b) the solid phase containing an antibody to the first hapten. The concentration of the bihapten (d) can be optimized within a concentration range to compete effectively with the analyte, FK778, and provide a good dose response curve without excessive predilution of the FK778 sample. The concentration of the conjugate (a) can be modulated downward by addition of unlabeled antibody, so as not to exceed the detection capability of a commercially available chemiluminescent reader. The ratio of the labeled antibody (a) to the unlabeled antibody (b) typically ranges from about 1:135 to about 1:225, and preferably is about 1:175.

In this aspect, the invention involves identifying a bihapten having the appropriate affinity for both an antibody to the first hapten and an antibody to FK778 or an analogue thereof in the bridging, i.e., bihapten, format. The compounds that are amenable to detection by the method and kit of the present invention include FK778, a slightly cross-reactive FK778 metabolite known as M3, and the active metabolite of leflunomide, known as A77 1726.

The method comprises the steps of:

(a) incubating a mixture comprising (1) a test sample suspected of containing FK778, (2) a solid phase coupled to an antibody specific for a first hapten, (3) a bihapten comprising the first hapten and FK778 or an analogue of FK778, and (4) a reagent mixture comprising an antibody to FK778 conjugated to a label and an antibody to FK778 not conjugated to a label to form a detectable complex comprising (i) the antibody to FK778 conjugated to the label, (ii) a bihapten comprising the first hapten and FK778 or an analogue of FK778, and (iii) the solid phase coupled to the antibody specific for the first hapten;

(b) separating the solid phase coupled to the antibody specific for a first hapten from the mixture;

(c) measuring the amount of label coupled to an antibody specific for FK778, which is bridged by a bihapten bound to an antibody specific for the first hapten that is bound to the solid phase; and (d) determining the amount of FK778 in the test sample from the amount of label measured.

A kit containing the reagents for carrying out the above-described assay comprises (a) a mixture of an antibody to FK778 conjugated to a label and an antibody to FK778 not conjugated to a label, (c) a bihapten comprising a first hapten and FK778 or an analogue of FK778, (b) a solid phase coupled to an antibody specific for the first hapten.

In another aspect, the method and kit involve the use of (a) antibody to FK778, (b) a bihapten comprising FK778 or an analogue of FK778 and a first hapten, e.g., a bihapten comprising the fluorescein hapten and the hapten of FK778 or an analogue of FK778, and (c) a pretreatment reagent.

The method of this aspect comprises the steps of:

(a) incubating a mixture comprising (1) a test sample suspected of containing FK778, (2) a diluent for the sample, if necessary, (3) a pretreatment reagent, (4) an antibody to FK778 or to an analogue of FK778, (5) a bihapten tracer comprising a first hapten and FK778 (or an analogue of FK778) to form a mixture comprising (i) unbound tracer, (ii) tracer bound to the antibody, (iii) FK778 bound to the antibody, and (iv) unbound FK778;

(b) measuring the ratio of tracer bound to the antibody and unbound tracer present by fluorescence polarization; and (c) determining the amount of FK778 or analogue of FK778 in the test sample from the fluorescence polarization signal measured.

The kit comprises (a) an antibody to FK778, (b) a bihapten tracer comprising a first hapten and FK778 or an analogue of FK778, (c) a pretreatment reagent.

Representative examples of hapten-containing derivatives of FK778 that are suitable for use in the present invention can have the following structural formulae:

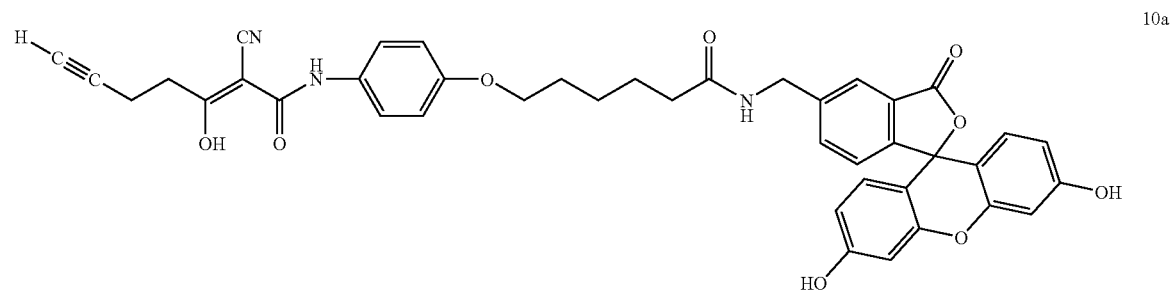
10a
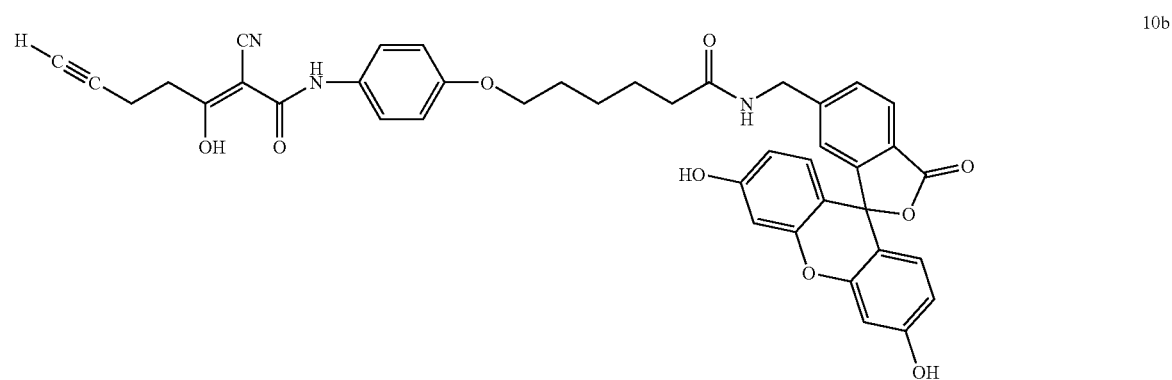
10b
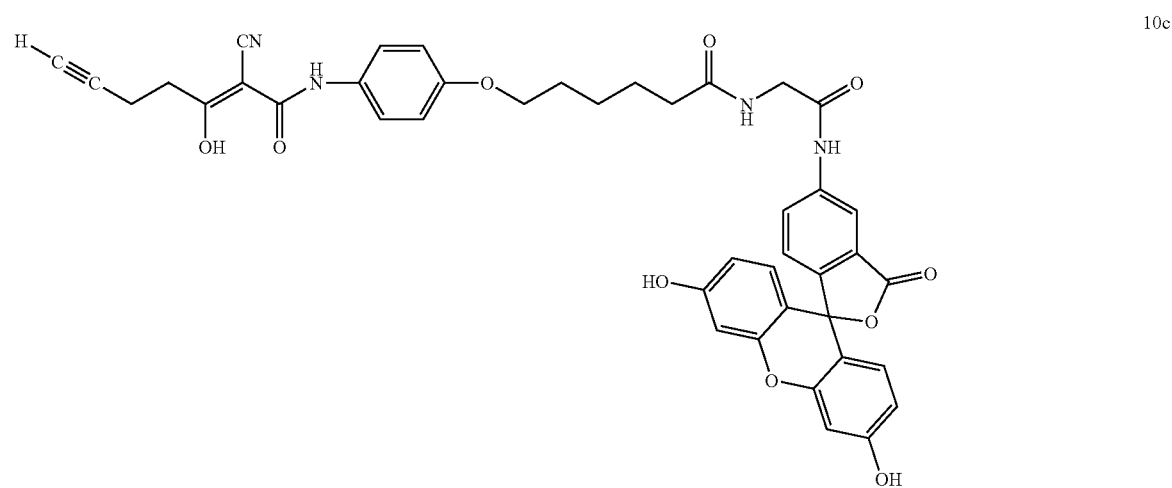
10c

-continued
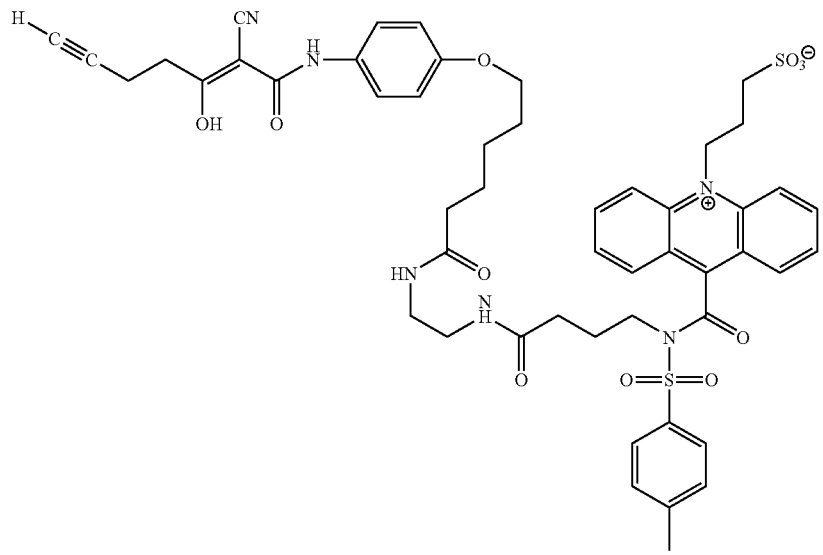
12
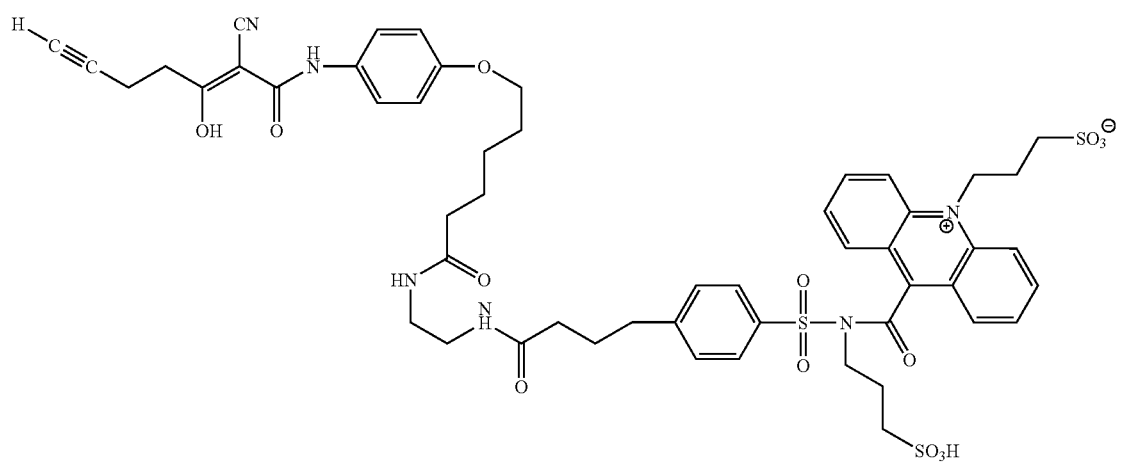
14
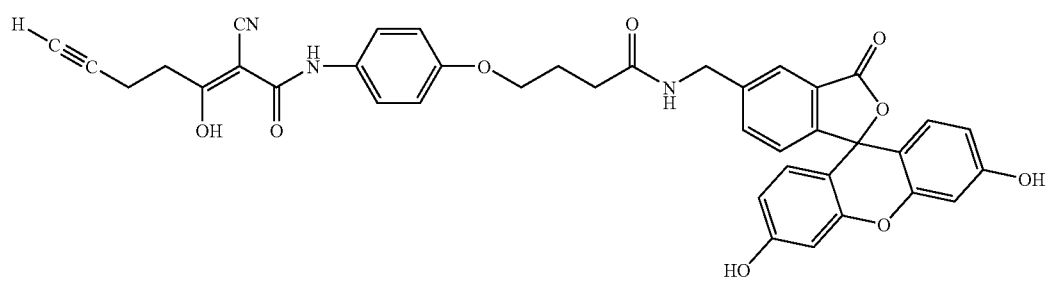
21a
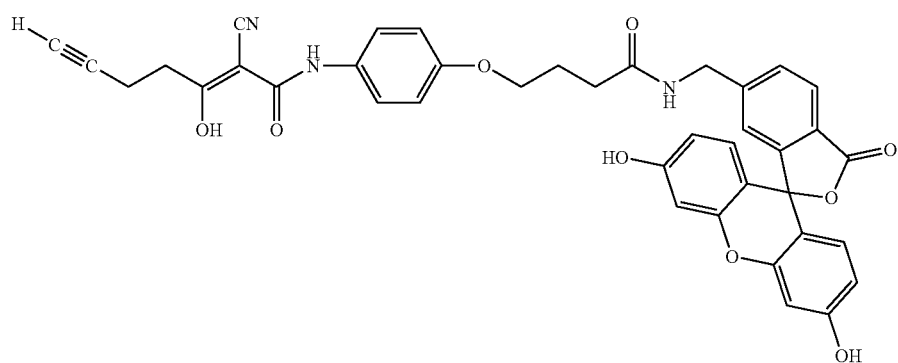
21b

-continued
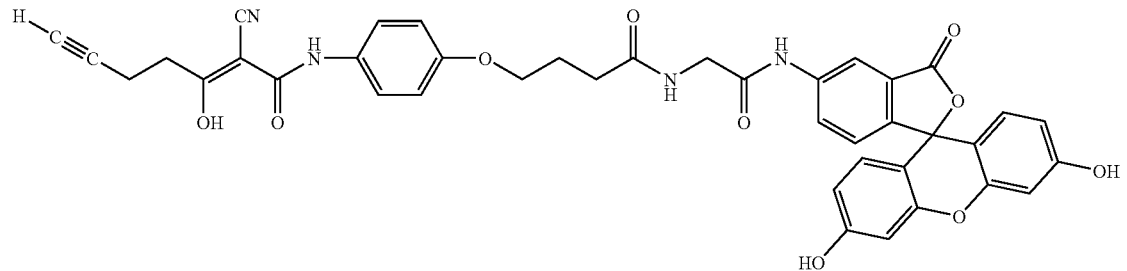
21c
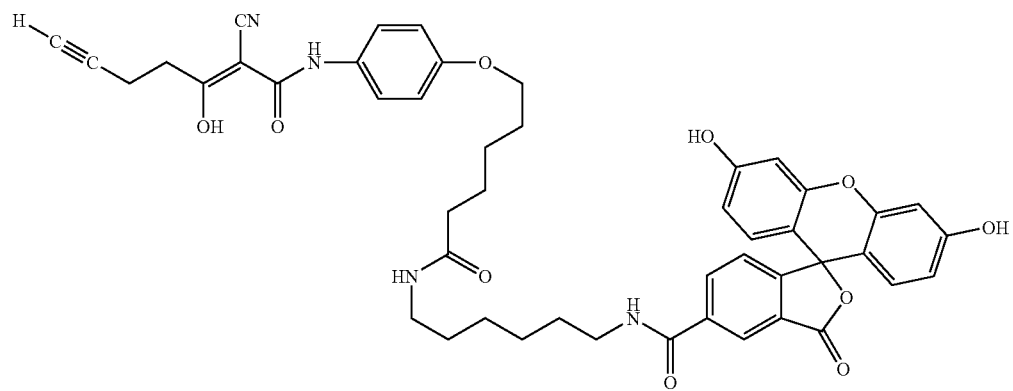
25a
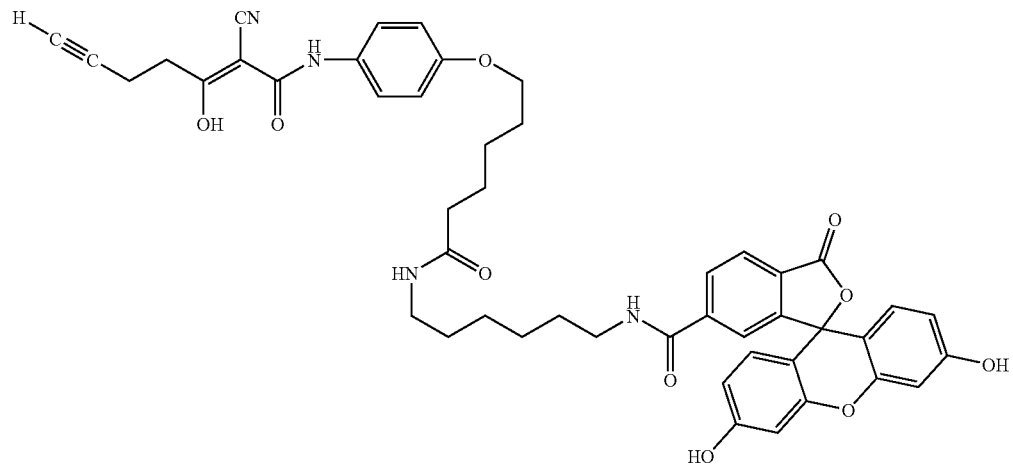
25b
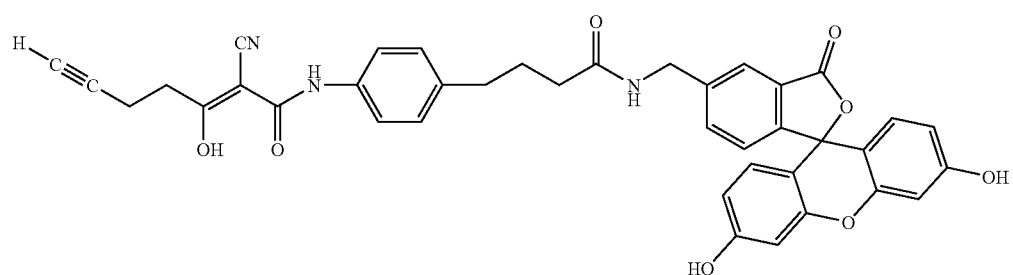
32a

-continued
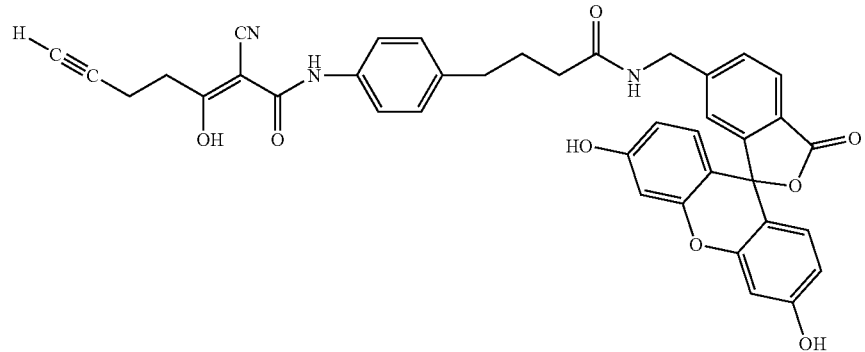
32b
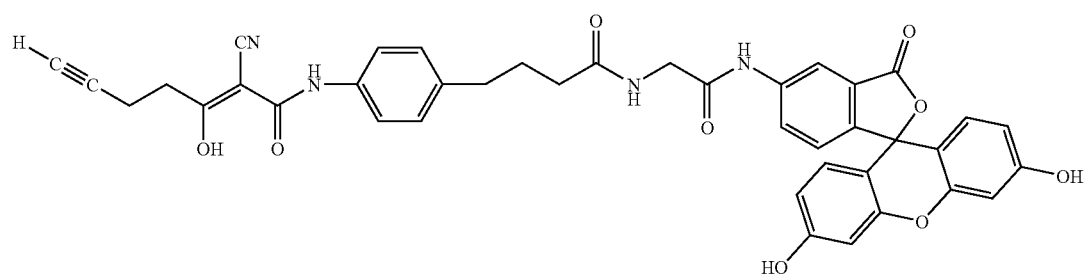
32c
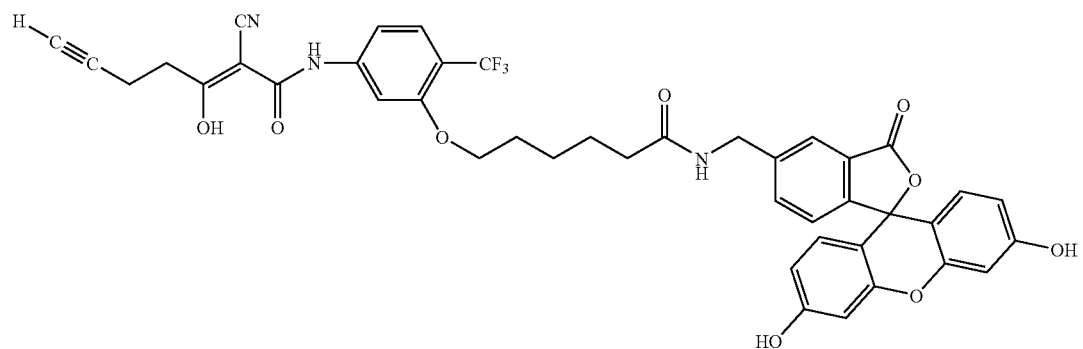
44a
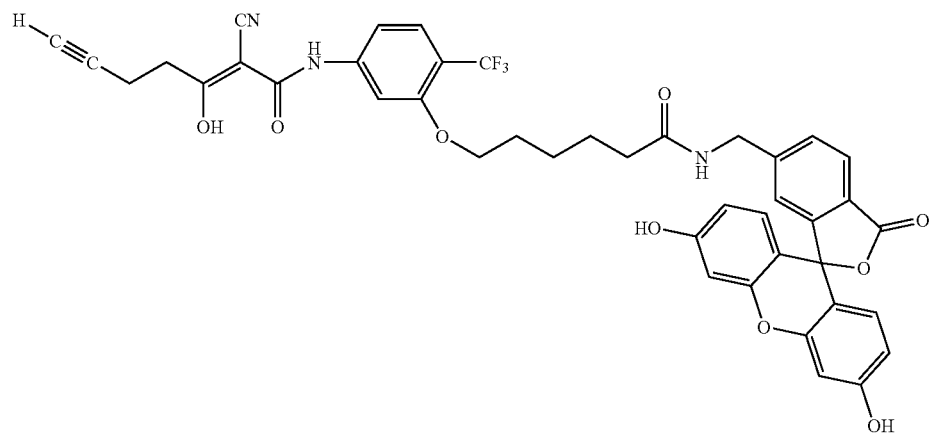
44b

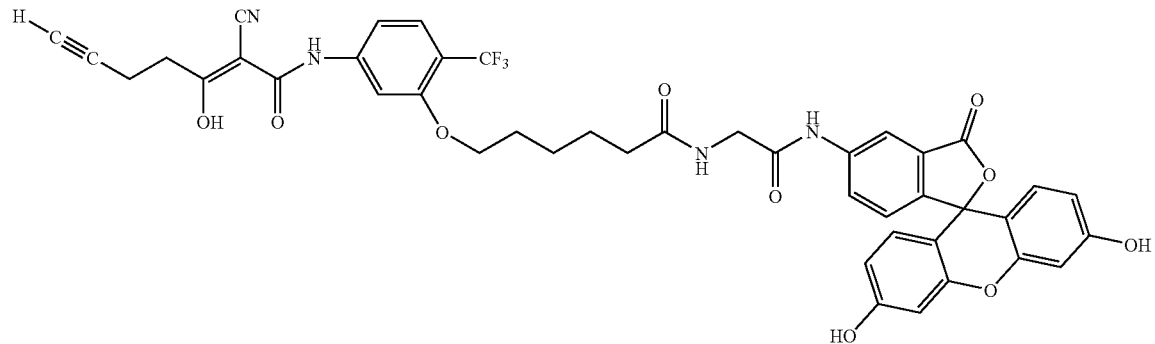
44c
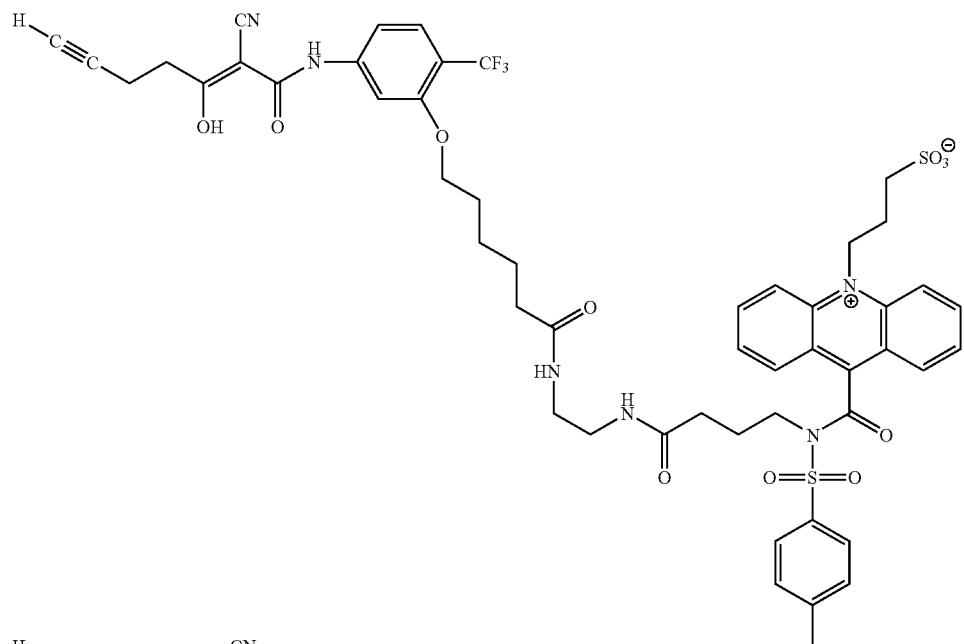
45
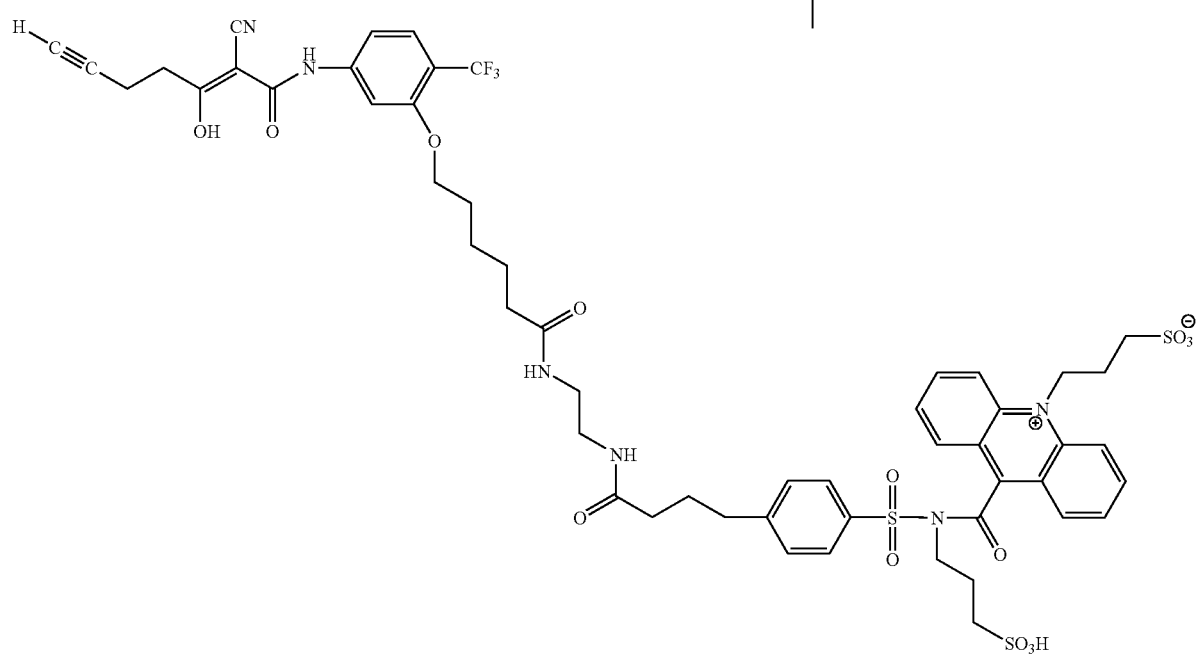
46

Structures 12, 14, 45, and 46 are tracers containing analogues of FK778 having acridinium labels and are not favored for an FK778 assay because of the excessively high signal that they generate in a conventional competitive immunoassay format. Structures 10b, 10c, 21a, 21b, 21c, 25a, 25b, 32a, 32b, and 32c are examples of fluorescein derivatives of FK778 in which the fluorescein molecule is coupled to the 4-position of the aromatic ring of the FK778 molecule. These bihapten tracers bind tightly to both antibodies to FK778 and antibodies to fluorescein and can be used as the bihapten comprising FK778 or an analogue of FK778 and the first hapten. Structures 44a, 44b and 44c are examples of fluorescein derivatives of FK778 in which the fluorescein molecule is coupled to the 3-position of the aromatic ring of the FK778 molecule, retaining the —$CF_3$ group at the 4-position. These structures can be used as the bihapten comprising FK778 or an analogue of FK778 and the first hapten so long as the antibody to FK778 has binding affinity for such derivatives.

It should also be noted that the FK778 moiety could be replaced by an analogue of the FK778 moiety when the measurement of the quantity of the analogue of FK778 is desired.

The primary benefit of the present invention is that the performance of a given assay format can be improved over that obtainable when it is used in a conventional assay format, i.e., when antibody to FK778 or analogue of FK778 is attached to the solid phase and the acridinium-containing tracer is used as the source of the signal.

The format of this assay enables it to be used in an automated analyzer. Furthermore the signal generating by the label can be confined to the range of analyzers that are commercially available.

BRIEF DESCRIPTION OF THE DRAWINGS

FIG. 1 is a schematic diagram illustrating one embodiment of the competitive assay of this invention. In this embodiment, a chemiluminescent label is used. In FIG. 1, the "Hot Antibody" is the antibody having the label and the "Cold Antibody" is the unlabeled antibody.

FIG. 4 is a flowchart illustrating a process for preparing conjugates of this invention. The conjugates employ a chemiluminescent label.

DETAILED DESCRIPTION

Figure 2:
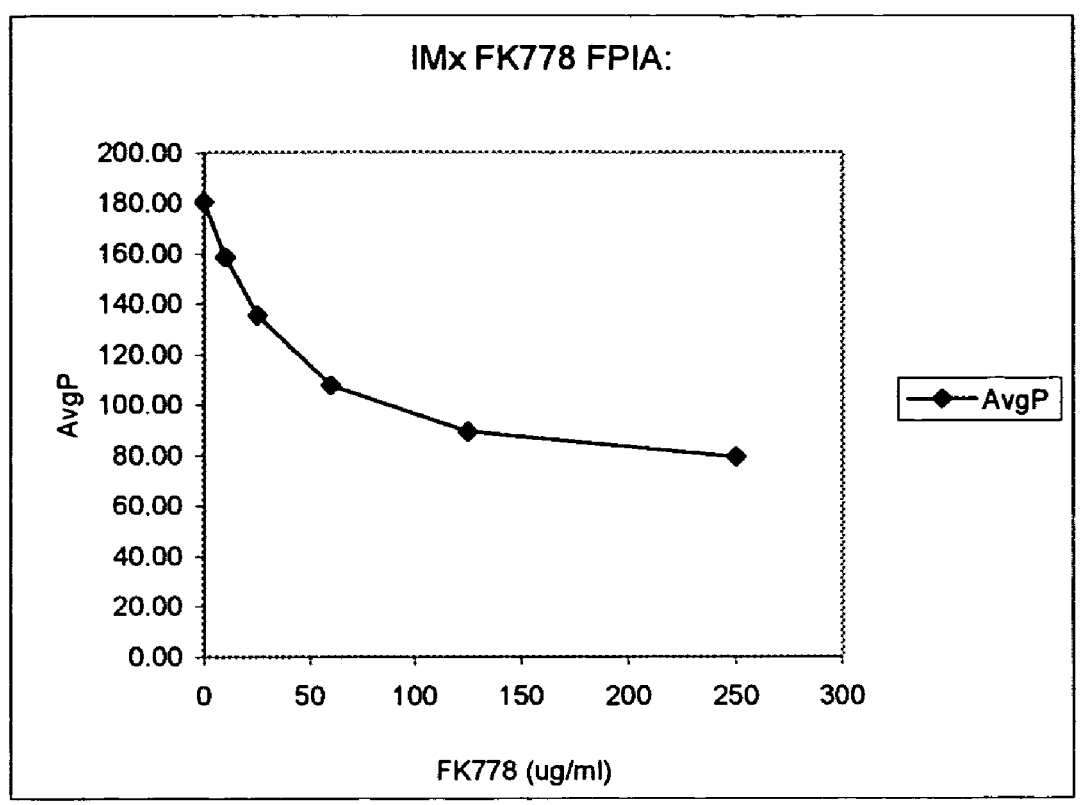
FIG. 2 is a graph illustrating the dose response curve generated by mixing FK778 with a fluorescein derivative of FK778 and an antibody to FK778 in a fluorescence polarization immunoassay.

As used herein, the term "label" means a moiety attached to an antibody or an analyte to render the reaction between the antibody and the analyte detectable. A label is capable of producing a signal that is detectable by visual or instrumental means. Various labels suitable for use in this invention include signal-producing substances such as chromogens, fluorescent compounds, chemiluminescent compounds, and the like. Representative examples of labels suitable for this invention include moieties that produce light, e.g., acridinium compounds, and moieties that produce fluorescence, e.g., fluorescein. The term "tracer" means an analyte conjugated to a label, such as, for example, FK778 conjugated to a fluorescein moiety, wherein the analyte conjugated to the label can effectively compete with the analyte, e.g., FK778, for sites on an antibody specific for the analyte.

The term "analogue" means a molecule having a structural similarity to an analyte. The term "derivative" means an analyte that has been chemically or biochemically modified, resulting in the addition or substitution of a chemical moiety, e.g., FK778 tracer or metabolite.

The expressions "sample", "test sample", and the like, as used herein, refer to a material suspected of containing the analyte. The test sample can be used directly as obtained from the source or following a pretreatment to modify the character of the sample. The test sample can be derived from any biological source, such as a physiological fluid, such as, for example, blood, saliva, ocular lens fluid, cerebral spinal fluid, sweat, urine, milk, ascites fluid, synovial fluid, peritoneal fluid, amniotic fluid, and the like. The test sample can be pretreated prior to use, such as preparing plasma from blood, diluting viscous fluids, and the like.

Methods of pretreatment can involve filtration, distillation, extraction, concentration, inactivation of interfering components, the addition of reagents, and the like.

As used herein, the term "anti FK778" means an antibody to FK778. As used herein, the term "CPSP" means 9-{N-Tosyl-N-(3-carboxypropyl)]-10-(3-sulfopropyl)acridinium carboxamide; the term "DMF" means dimethyl formamide. As used herein, the expression "acridinium incorporation ratio" means the ratio of acridinium molecules per labeled antibody molecule. As used herein, the expression "overcoat buffer" means a solution containing buffer and a non-specific protein, e.g., bovine serum albumin, used to treat microparticles after the microparticles are coated with a specific protein, such as an antibody.

The antibody-coated microparticles can be prepared by procedures that are well known to one of ordinary skill in the art. The conjugate is preferably prepared by coupling an activated form of the label, e.g., an active ester, to the antibody. For the sake of brevity, only the competitive immunoassay techniques involving a chemiluminescent assay and a fluorescence polarization immunoassay will be described in detail.

In the aspect of this invention that employs a chemiluminescent label, the method of the present invention comprises the steps of:

(a) incubating a mixture comprising (1) a test sample suspected of containing FK778, (2) a solid phase coupled to an antibody specific for a first hapten, (3) a bihapten comprising the first hapten and FK778 or an analogue of FK778, and (4) a reagent mixture comprising an antibody to FK778 conjugated to a label and an antibody to FK778 not conjugated to a label to form a detectable complex comprising (i) the antibody to FK778 conjugated to the label, (ii) a bihapten comprising the first hapten and FK778 or an analogue of FK778, and (iii) the solid phase coupled to the antibody specific for the first hapten;

(b) separating the solid phase coupled to the antibody specific for the first hapten from the mixture;

(c) measuring the amount of label coupled to the antibody specific for FK778, which is bridged by a bihapten to an antibody specific for a hapten that is bound to the solid phase; and (d) determining the amount of FK778 in the test sample from the amount of label measured.

A kit containing the reagents for carrying out the above-described assay comprises (a) a mixture of an antibody to FK778 conjugated to a label and an antibody to FK778 not conjugated to a label, (b) a bihapten comprising a first hapten and FK778 or an analogue of FK778, and (c) a solid phase coupled to an antibody specific for the first hapten.

FIG. 1 illustrates one embodiment of the above-described assay in schematic form. According to FIG. 1, a prediluted sample (10 μL quantity of a 1:20 dilution of the sample) is mixed with line diluent (50 μL) and a reagent mixture comprising an antibody to FK778 conjugated to an appropriate label and an unlabeled antibody to FK778 (90 μL, ratio of antibody conjugated to a label to antibody not conjugated to a label is 1:150). The resulting mixture is preincubated for approximately six (6) seconds. The resulting mixture (150 μL) is mixed with the bihapten reagent (50 μL) and the solid phase (50 μL). The resulting mixture is incubated for approximately 25 minutes and washed to form a signal generating complex comprising (i) solid phase containing an antibody to fluorescein, (ii) bihapten comprising FK778 and fluorescein and (iii) an antibody to FK778 conjugated to a label.

Binding members specific for FK778 include anti-FK778 specific binding proteins, such as, for example, monoclonal antibodies, and other specific synthetic or recombinant proteins that specifically bind FK778. For example, it is well known by those skilled in the art that monoclonal antibodies that specifically bind to FK778 can be produced. When an immunogen comprising FK778 or a derivative of FK778 coupled to a carrier protein (e.g., albumin), typically by a covalent bond, is injected into an animal, the animal's immune system will produce antibodies that specifically bind to FK778. General methods for the preparation of monoclonal antibodies to analytes using mice or rats are well known to those skilled in the art. More recently methods for preparing synthetic and recombinant proteins specific for analytes have been reported, and the same methods can be readily adapted to the preparation of synthetic and recombinant proteins specific for FK778. Fujisawa has developed a monoclonal antibody to FK778 that is useful in this invention. This antibody is referred to as clone 20A1. The antibody used in the development of the FK778 assay is a subclone referred to as 20A1 sc241.

Preferably, the signal is measured by using a solid phase having a binding member specific for a hapten bound thereto. An example of a solid phase is a microparticle. The solid phase and the test sample are separated so that the amount of labeled conjugate bound to the solid phase or the amount of labeled conjugate remaining in solution can be determined. The amount of labeled conjugate bound to the solid phase or the amount of labeled conjugate remaining in solution can be determined by chemiluminescence, wherein a chemiluminescent moiety is used as the label in the conjugate. The chemiluminescent moiety can be converted into a light-emitting compound by an appropriate trigger reagent. The amount of chemiluminescent compound formed is an indication of the quantity of FK778 analyte present in the reaction mixture. Thus, the measurement of chemiluminescence can be used to determine to the quantity of FK778 present in the test sample. The amount of labeled conjugate on the solid phase or in solution can be correlated to the concentration of FK778 in the test sample by means of a plot showing chemiluminescent activity as a function of concentration of FK778, typically referred to as a standard curve.

A standard curve can be prepared by performing the assays using six calibrators such as those set forth in TABLE XVI, which will be discussed later. Controls are measured to verify that the standard curve is valid. When a sample having an unknown FK778 level is assayed, the measured assay signal is compared to the standard curve, and the FK778 level corresponding to the measured signal is the FK778 level of the sample.

A solid phase according to the present invention can be a mixture of microparticles with binding members specific for a first hapten chemically or physically bound to the microparticles. Microparticles that can be used in this invention can be made of polymeric material, and more preferably include microparticles derived from polymers having styrene units or polymers having acrylate units. A method for separating these particles from the test sample involves capture of the microparticle on a porous matrix, such as a glass fiber.

A preferred solid phase that can be used include a mixture of magnetizable microparticles having binding members specific for the first hapten chemically or physically bound to the microparticles. Magnetizable microparticles that are useful in this invention preferably have ferric oxide or chromium oxide cores and a polymeric coating. Such coatings are preferably made from homopolymers and copolymers having styrene units, homopolymers and copolymers having carboxylated styrene units, or homopolymers and copolymers having acrylate or methacrylate units. The microparticles are preferably substantially spherical and preferably have radii ranging from about 1 μm to about 10 μm, preferably from about 4 μm to about 5 μm.

The bihapten is bound to the antibody immobilized on the solid phase by means of interaction of a hapten with the antibody to that hapten immobilized on the solid phase. The bihapten should be bound to the solid phase in such a way that substantially none of the specific binding members detach during the subsequent reactions and wash steps. Regardless of the specific coupling method selected, the bihapten must be able to bind to the antibody to the first hapten and, after being coupled to the solid phase, to the antibody conjugated to the label.

Other solid phases that are known to those skilled in the art include the walls of wells of reaction trays, tubes, polymeric beads, to nitrocellulose strips, membranes, and the like. Natural, synthetic, and naturally occurring materials that are synthetically modified can be used as the material of the solid phase. Such materials include polysaccharides, e.g., cellulosic materials, such as, for example, paper and cellulosic derivatives, such as cellulose acetate and nitrocellulose; silica; inorganic materials, such as, for example, deactivated alumina. diatomaceous earth, $MgSO_4$, or other inorganic finely divided material uniformly dispersed in a porous polymeric matrix, wherein the matrix may comprise one or more polymers such as homopolymers and copolymers of vinyl chloride, e.g., polyvinyl chloride, vinyl chloride propylene copolymer, and vinyl chloride-vinyl acetate copolymer, both, both naturally occurring (e.g. cotton) and synthetic (e.g., nylon); porous gels, such as silica gel, agarose, dextran, and gelatin; polymeric films, such as polyacrylamide; and the like. In any case, the solid phase should have sufficient strength to maintain the desired physical shape and should not interfere with the production of a detectable signal. Strength can be provided by means of a support.

In one embodiment, the signal can be detected by using an ARCHITECT® automated analyzer (Abbott Laboratories, Abbott Park, Ill.). This analyzer contains an optical assembly comprising a photomultiplier to measure light. This instrument is described in U.S. Pat. Nos. 5,795,784 and 5,856,194, both of which are incorporated herein by reference. In another embodiment, the signal can be detected by using an IMx® automated analyzer (Abbott Laboratories, Abbott Park, Ill.). This analyzer contains an optical assembly comprising a fluorescence polarization spectrophotometer that uses a xenon bulb as its light source. This instrument is described in U.S. Pat. No. 5,294,404, incorporated herein by reference.

In the aspect of this invention that employs a fluorescent label, the method and kit involve the use of (a) an antibody to FK778, (b) a bihapten comprising FK778 or an analogue of FK778 and a first hapten, e.g., a tracer comprising a fluorescein hapten and FK778 hapten, and (c) a pretreatment reagent. The bihapten provides a fluorescence polarization signal that can distinguish between tracer not bound to the antibody and tracer bound to the antibody.

The method of this aspect comprises the steps of:

(a) incubating a mixture comprising (1) a test sample suspected of containing FK778, (2) an antibody to FK778 or to an analogue of FK778, (3) a pretreatment reagent, (4) a diluent for the sample, if necessary, (5) a bihapten tracer comprising a first hapten and FK778 (or an analogue of FK778) to form a mixture comprising (i) unbound tracer, (ii) tracer bound to the antibody, (iii) FK778 bound to the antibody, and (iv) unbound FK778;

(b) measuring the amount of tracer bound to the antibody and unbound tracer by fluorescence polarization; and (c) determining the amount of FK778 or the analogue of FK778 in the test sample by the fluorescence polarization signal measured.

The kit comprises (a) an antibody to FK778, (b) a bihapten comprising a first hapten and FK778 or an analogue of FK778, and (c) a pretreatment reagent.

The standard curve that relates the assay signal to FK778 concentration is generally prepared from calibrator solutions containing known concentrations of FK778. Preferably, six calibrators are used to obtain a calibration curve, though more or fewer calibrators can be used, depending on the accuracy and precision of the result desired. Preferably, the calibrators contain increasing amounts of FK778. The FK778 calibrators used in these studies contain 4% bovine serum albumin and an antimicrobial agent in a Tris buffer at pH 7.4. Controls are generally used in conjunction with an assay to confirm the validity of a calibration curve or assay reagents. The formulation of the controls may be different from that of the calibrators, and the concentration of FK778 of a given control may not be identical with that of any one of the calibrators. For example, controls having concentrations of FK778 of 20, 75, and 150 μg/mL would be suitable controls for the calibrators in TABLE XVI. One of ordinary skill in the art would be capable of devising other calibrator and control formulations.

To maintain aseptic conditions throughout the procedure, it may be desirable to add small quantity of an antimicrobial agent to the system, which may include solvents, antibiotics, and poisons.

The following reaction schemes illustrate the synthesis of 4-O-alkylcarboxyphenyl FK778 haptens and preparation of fluorescein and chemiluminescent tracers from these haptens. Symbols in the reaction schemes are listed below:

DMF: Dimethylformamide

THF: Tetrahydrofuran

Boc: tert-Butoxycarbonyl

NaH: Sodium hydride

TFA: Trifluoroacetic acid

LiOH: Lithium hydroxide

HOBt: 1-Hydroxybenzotriazole

EDAC: 1-(3-Dimethylaminopropyl)-3-ethylcarbodiimide hydrochloride

NHS: N-Hydroxysuccinimide

MeOH: Methanol

Et$_3$N: Trimethylamine

K$_2$CO$_3$: Potassium carbonate

CH$_2$Cl$_2$: Dichloromethane

NaNO$_2$: Sodium nitrite

KI: Potassium iodide

CF$_3$I: Trifluoromethyl iodide

Cu: Copper powder

Pt/C: Platinum on carbon

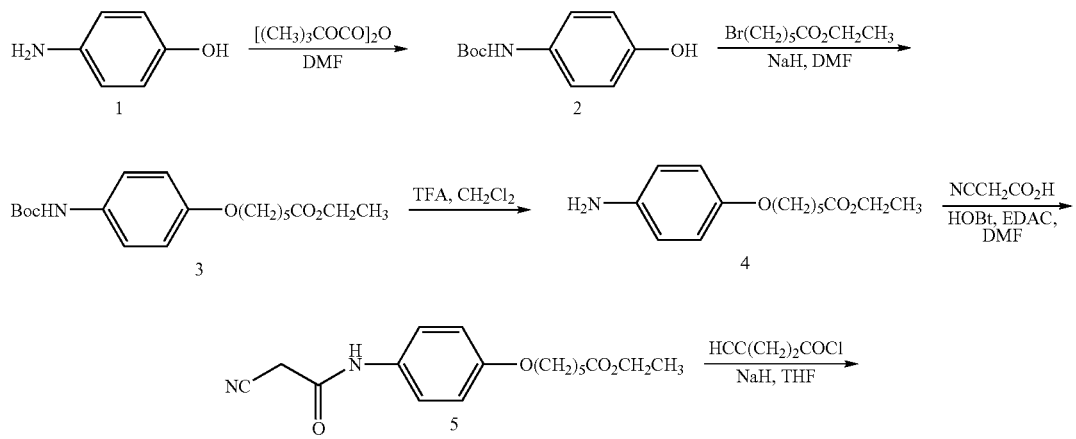

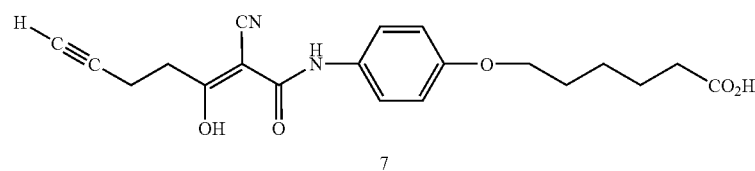

-continued

7

Scheme 2: Synthesis of FK778-containing fluorescent tracers (10a-10c) from 4-O-pentylcarboxyphenyl hapten (7)

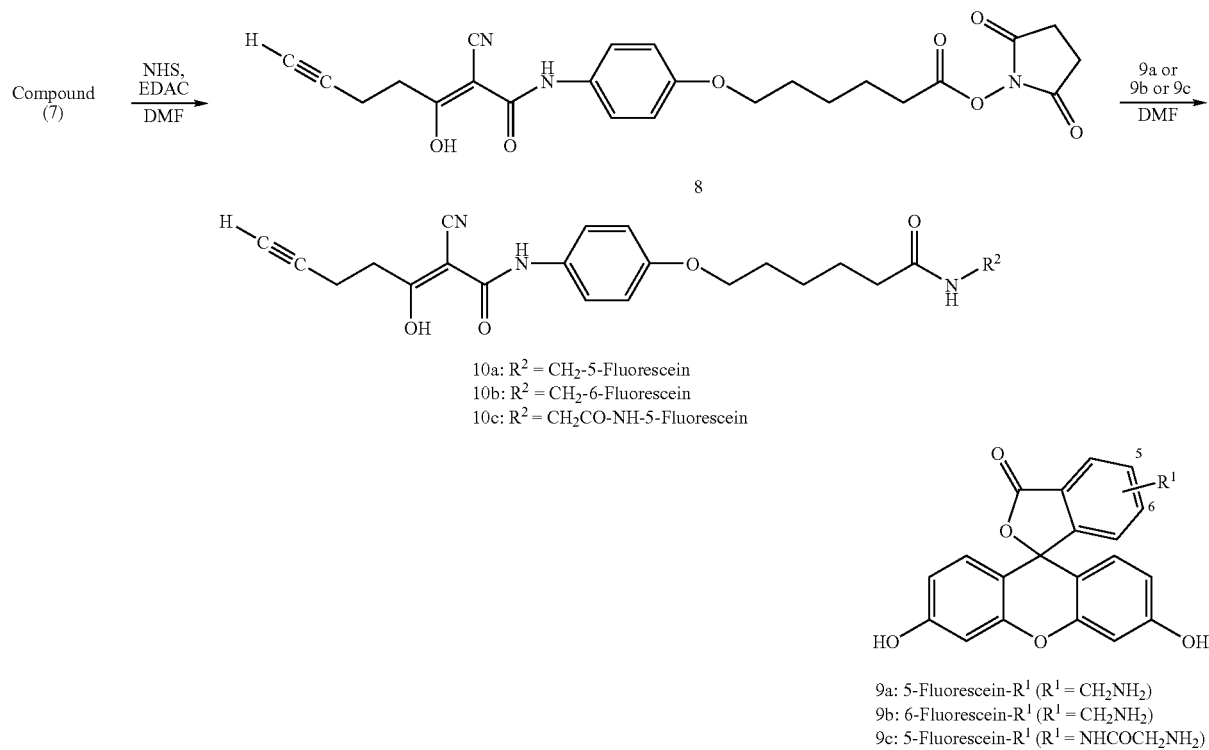

10a: $R^2$ = $CH_2$-5-Fluorescein
10b: $R^2$ = $CH_2$-6-Fluorescein
10c: $R^2$ = $CH_2CO$-NH-5-Fluorescein 9a: 5-Fluorescein-$R^1$ ($R^1$ = $CH_2NH_2$)
9b: 6-Fluorescein-$R^1$ ($R^1$ = $CH_2NH_2$)
9c: 5-Fluorescein-$R^1$ ($R^1$ = $NHCOCH_2NH_2$)

Scheme 3: Synthesis of FK778-containing chemiluminescent tracers (12 and 14) from Compound 8

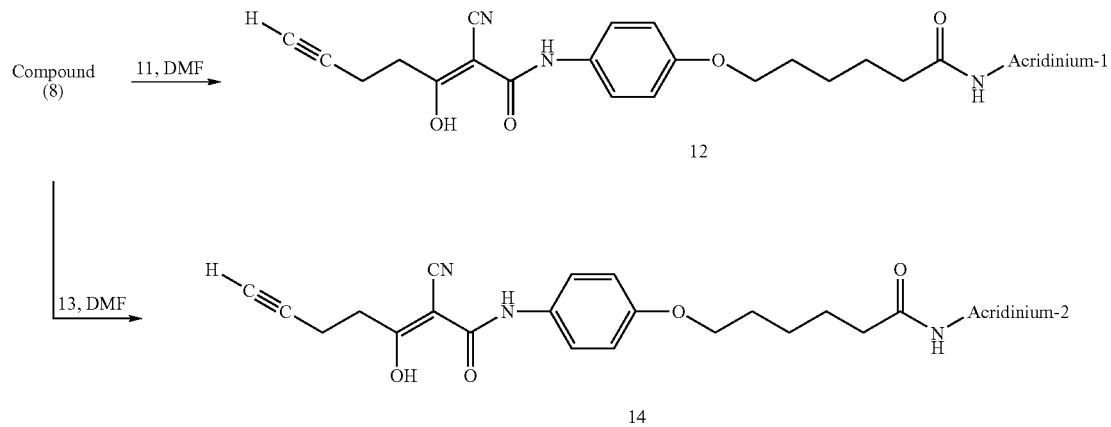

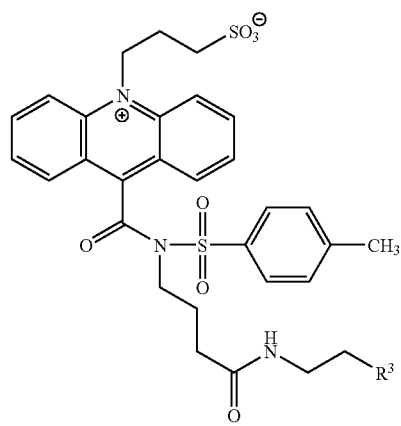
11: 1-Acridinium-R³ (R³ =NH₂)
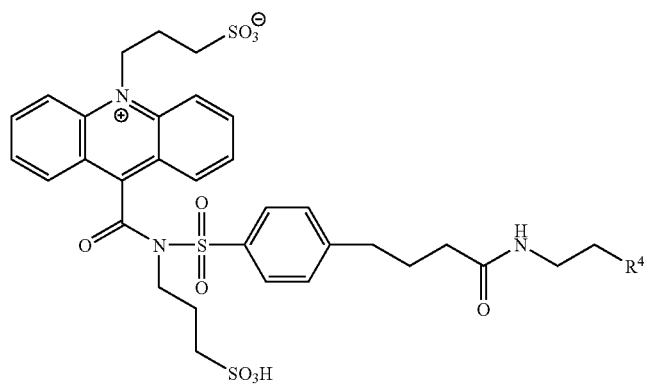
13: 2-Acridinium-R⁴ (R⁴ =NH₂)
Scheme 4: Synthesis of 4-O-propylcarboxyphenyl hapten of FK778 (19)
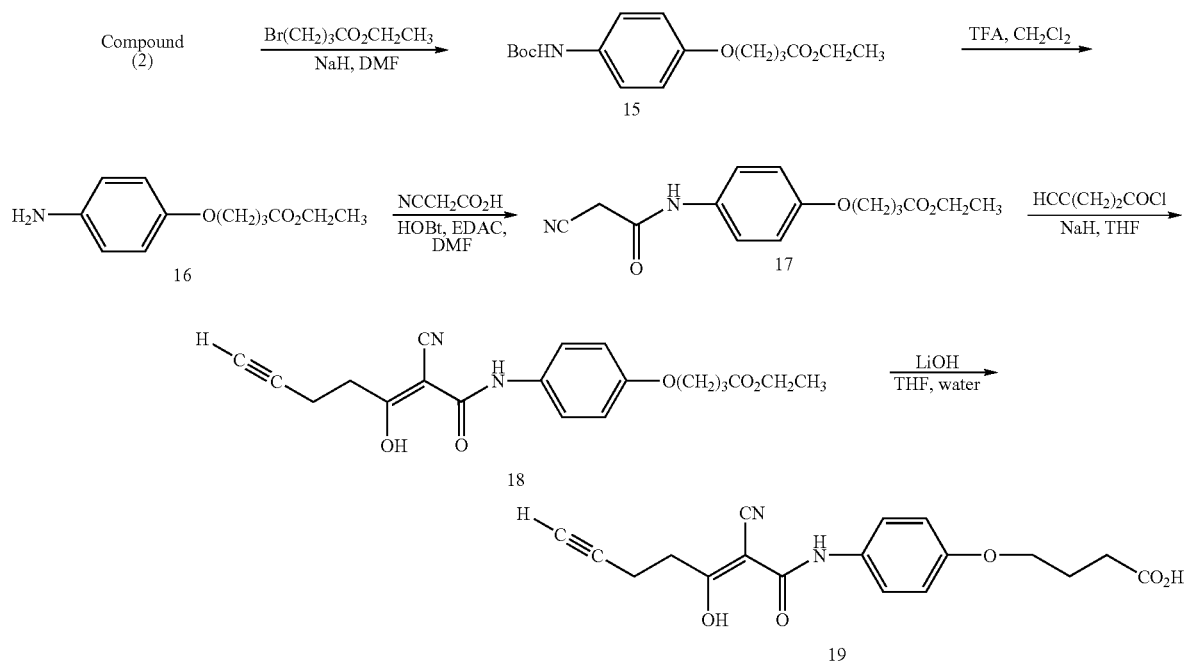
Scheme 5: Synthesis of FK778-containing fluorescent tracers (21a-21c) from 4-O-propylcarboxyphenyl hapten (19)
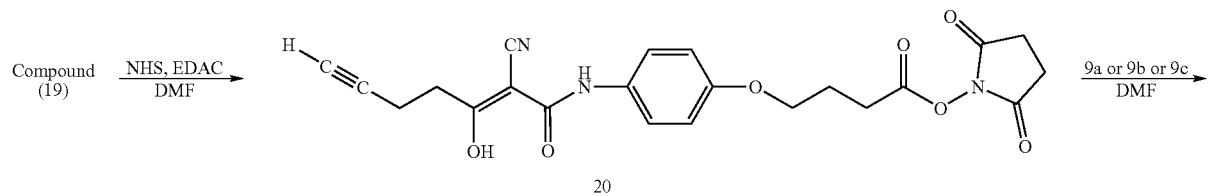

-continued

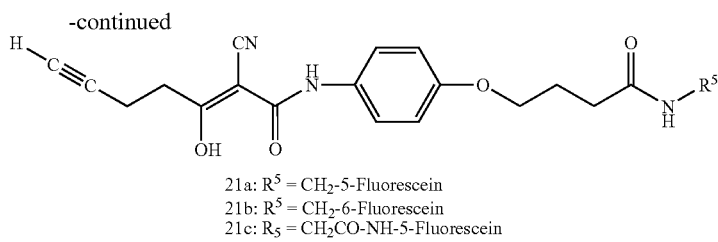

21a: $R^5$ = $CH_2$-5-Fluorescein
21b: $R^5$ = $CH_2$-6-Fluorescein
21c: $R_5$ = $CH_2CO$-NH-5-Fluorescein

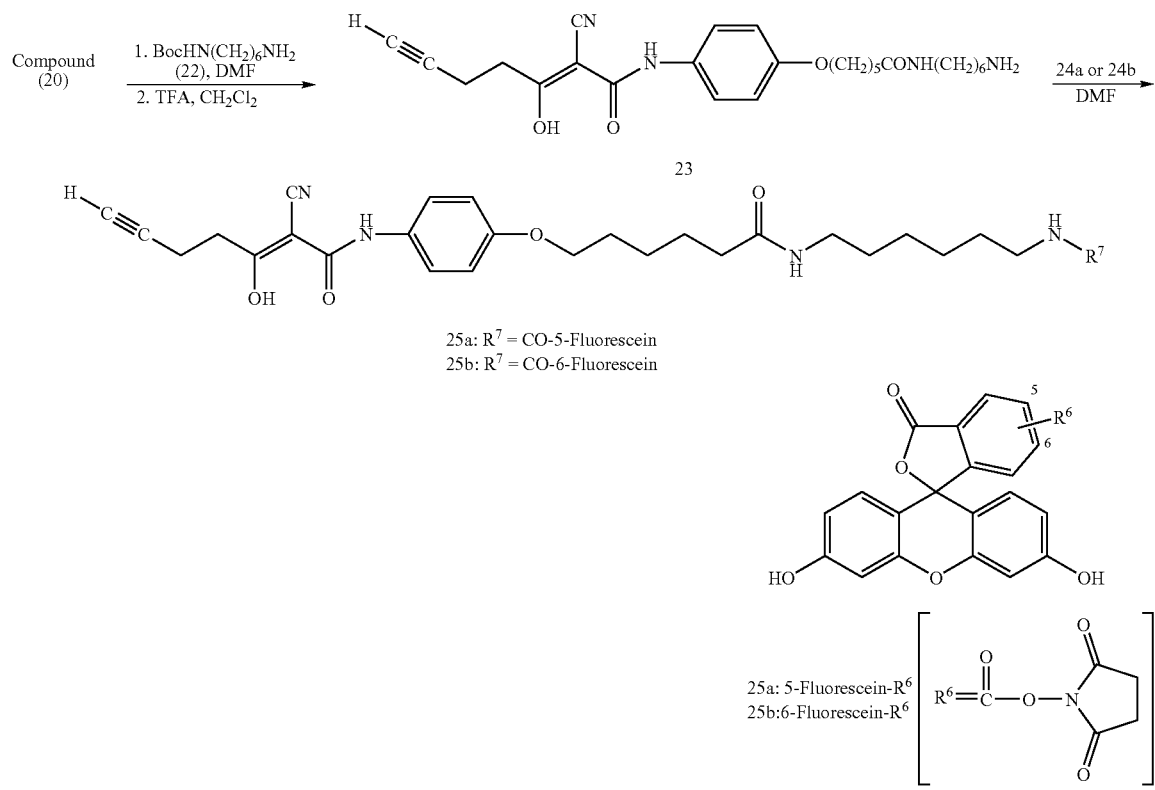

Scheme 6: Synthesis of FK778-containing fluorescent tracers (25a and 25b) from Compound 20

25a: $R^7$ = CO-5-Fluorescein
25b: $R^7$ = CO-6-Fluorescein

25a: 5-Fluorescein-$R^6$
25b: 6-Fluorescein-$R^6$

The following reaction schemes illustrate synthesis of 3-propylcarboxyphenyl FK778 hapten and preparation of fluorescein tracers from that hapten.

Scheme 7: Synthesis of 4-propylcarboxyphenyl hapten of FK778 (30)

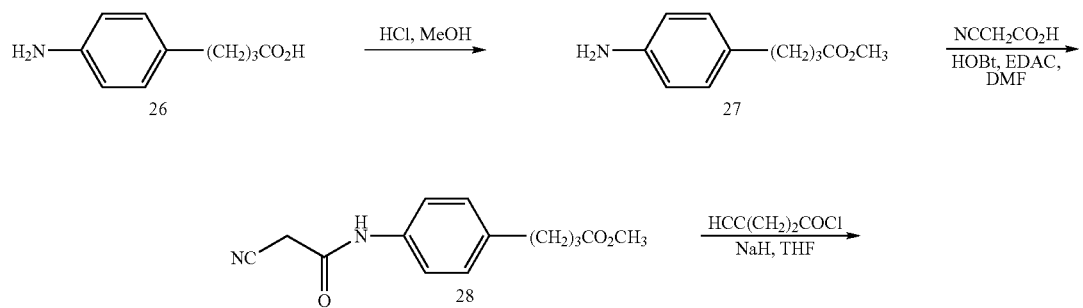

-continued
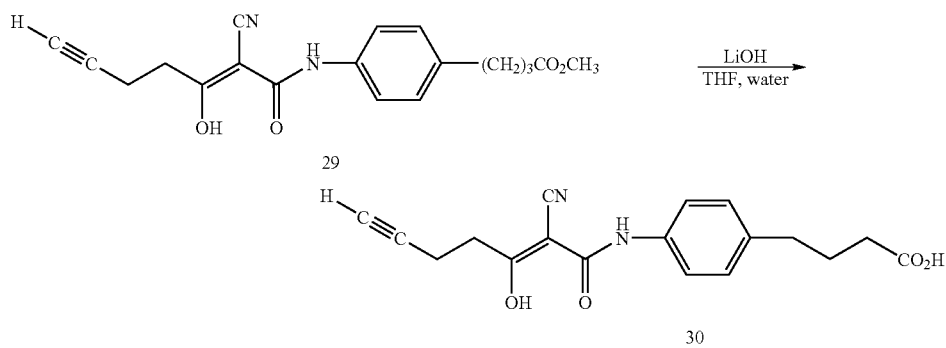
Scheme 8: Synthesis of FK778-containing fluorescent tracers (32a-32c) from 4-propylcarboxyphenyl hapten (30)
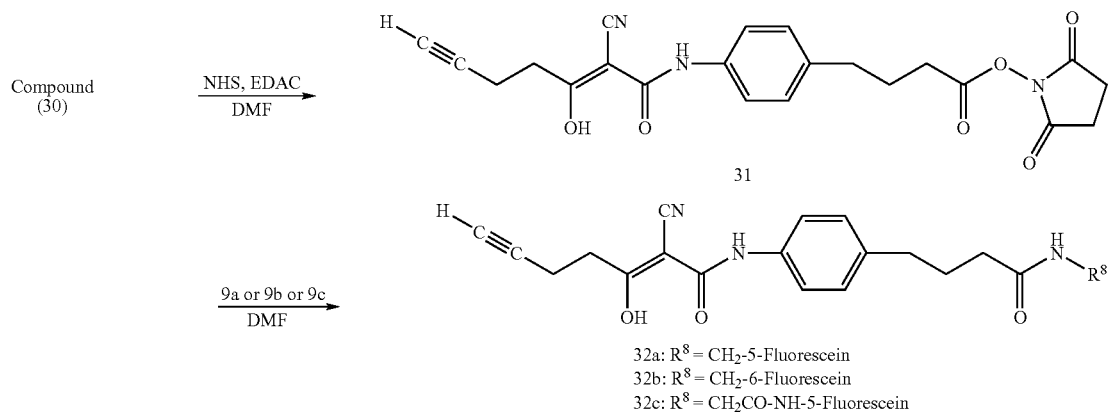
32a: $R^8$ = $CH_2$-5-Fluorescein
32b: $R^8$ = $CH_2$-6-Fluorescein
32c: $R^8$ = $CH_2CO$-NH-5-Fluorescein
Scheme 9: Synthesis of 3-O-pentylcarboxyphenyl hapten of FK778 (42)
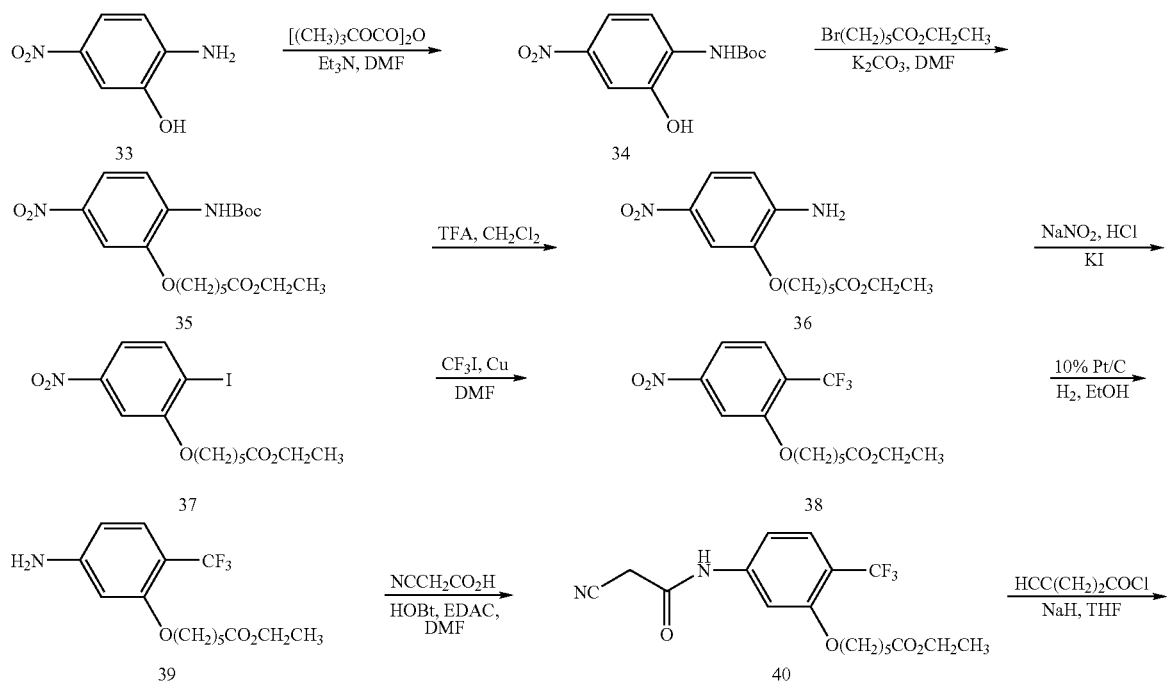

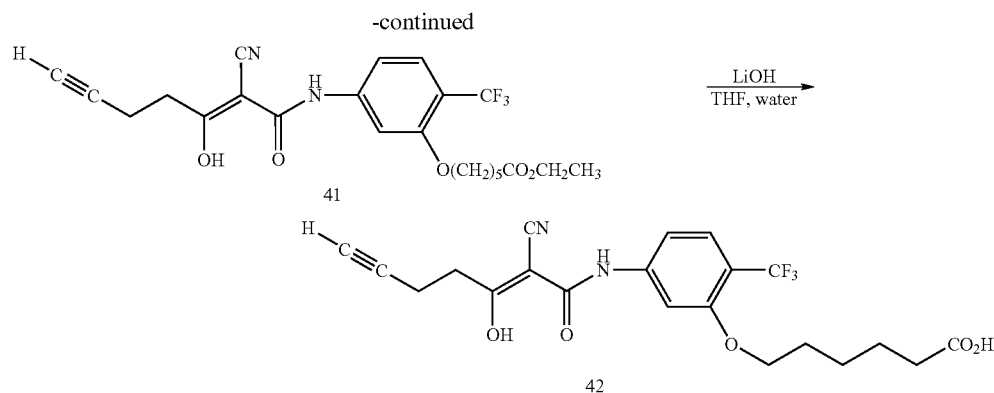
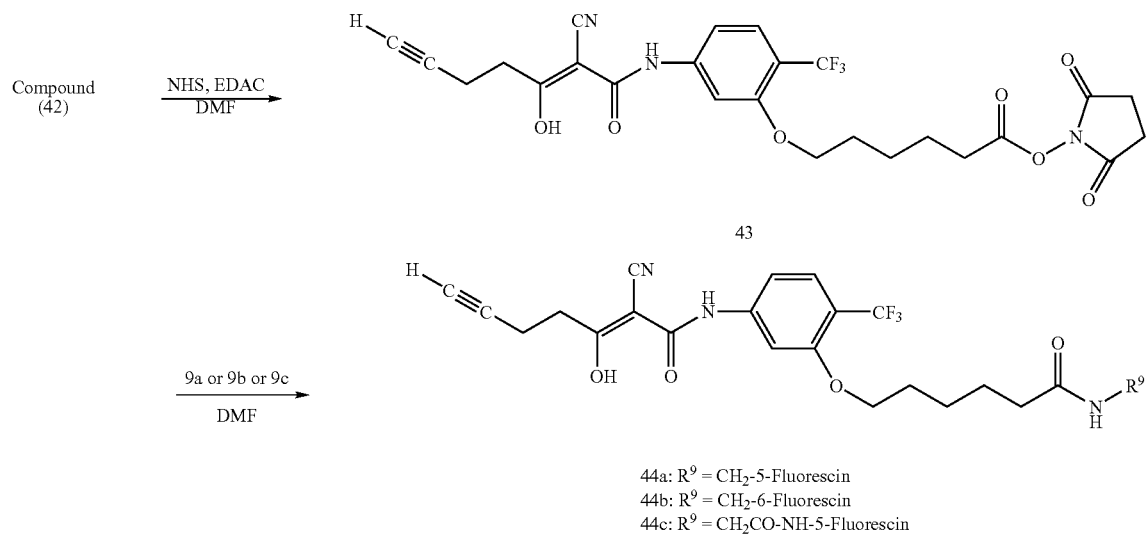
Scheme 10: Synthesis of FK778-containing fluorescent tracers (44a-44c) from 3-O-pentylcarboxyphenyl hapten (42)
44a: $R^9$ = $CH_2$-5-Fluorescin
44b: $R^9$ = $CH_2$-6-Fluorescin
44c: $R^9$ = $CH_2CO$-NH-5-Fluorescin
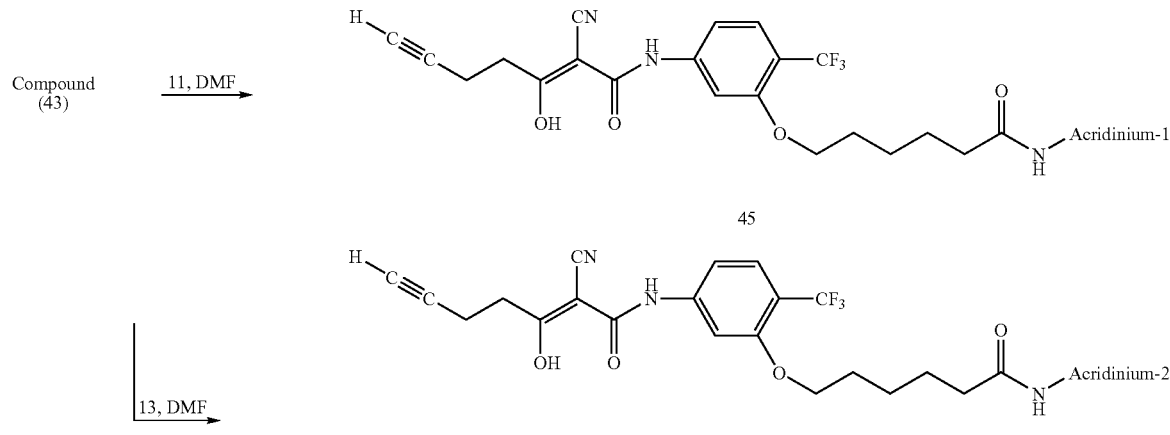
Scheme 11: Synthesis of FK778 chemiluminescent tracers (45 and 46) from Compound 43

The following examples are illustrative of the invention and are not to be interpreted as limiting the scope of the invention, as defined in the claims. All percentages are by grams (g) weight per 100 milliliters (mL), volume (w/v), unless otherwise indicated.

EXAMPLE 1

FK778 assays were performed by an ARCHITECT® instrument, commercially available from Abbott Laboratories, Abbott Park, Ill., according to the following procedure. See also U.S. Pat. Nos. 5,795,784 and 5,856,194, both of which are incorporated herein by reference. A serum sample (10 μL) was diluted with Line Diluent at a ratio of 1 part sample to 20 parts Line Diluent. A portion of the diluted sample (10 μL) was mixed with 90 μL of Conjugate Reagent and 50 μL of Line Diluent. Magnetic Microparticle Reagent (50 μL) and Bihapten Tracer Reagent (50 μL) were added to the foregoing mixture after a period of six (6) seconds. The resulting mixture (250 μL) was incubated for 25 minutes. The microparticles were washed three (3) times with 1 mL of Line Diluent. The magnetic particles were attracted to a magnet at the same time that they were being washed. The washed microparticles were treated with Pretrigger Reagent (100 μL acidic hydrogen peroxide). Finally, the chemiluminescent reaction was triggered by addition of Trigger Reagent (alkaline detergent solution (300 μL)). Measurement of light generated was carried out by means of a photomultiplier tube.

Materials needed for the assay, including wash buffer, Pretrigger Reagent, Trigger Reagent, and ARCHITECT® instruments are available commercially from Abbott Laboratories, Abbott Park, Ill. TABLE I shows the compositions of a representative examples of components suitable for the assay of this invention.

TABLE I

| Line Diluent | Conjugate Reagent | Magnetic Microparticle Reagent | Bihapten Tracer Reagent |
|---|---|---|---|
| Sodium Phosphate Buffer, pH 7.2 | MES Buffer, pH 5.6 | Bis-Tris-HCl Buffer, pH 6.5 | Tris Buffer, pH 7.4 |
| Sodium Chloride | Acridinium labeled antibody to FK778 | Magnetic microparticles coated with antibody to fluorescein | Tracer comprising FK778 and fluorescein |
| Antimicrobial agent | Unlabeled antibody to FK778 | Bovine gamma globulin | Bovine serum albumin |
| Detergent | Mouse IgG | Mouse IgG | Triton ® X-100 detergent |
|  | Bovine serum albumin | Sodium chloride |  |
|  | Antifoam agent | Antifoam agent | Antifoam agent |

Antifoam agent prevents reagent foaming during handling and can improve on-board reagent stability. TABLE II shows a composition for a Conjugate Reagent suitable for use in this invention.

TABLE II

| Ingredient | Concentration | Molecular weight (approximate) | Final concentration in reagent |
|---|---|---|---|
| CPSP conjugated antibody (0.25 IR) | 0.3 μg/mL | 75,000 per binding site | 1.4 nM |
| Unlabeled antibody (binding sites) | 11 μg/mL | 75,000 per binding site | 52.8 nM |
| Bovine serum albumin | 1 μg/mL | 68,000 | 5.3 μM |
| Mouse IgG | 100 μg/mL | 150,000 | 0.13 μM |
| Antimicrobial agent (2-Methyl-4-isothiazolin-3-one) | 7 μg/mL | 115 | 22 μM |
| Antimicrobial agent (5-Chloro-2-methyl-4-isothiazolin-3-one) | 23 μg/mL | 151 | 55 μM |
| 50 mM MES buffer, pH 5.6 | 9.75 g/L | 195 | 18 μM |
| 150 mM NaCl | 8.77 g/L | 58 | 54 μM |
| Antifoam agent | 100 μg/mL | N/A | 36 μg/mL |

TABLE III shows a composition for the Magnetic Microparticle Reagent suitable for use in this invention.

TABLE III

| Ingredient | Concentration | Molecular weight (approximate) | Final concentration in reagent |
|---|---|---|---|
| Microparticle, anti FITC sites | 50 nM | N/A | 10 nM |
| Bovine gamma globulin | 1 mg/mL | 150,000 | 1.33 μM |
| Mouse IgG | 100 μg/mL | 150,000 | 0.13 μM |
| Antimicrobial agent (2-Methyl-4-isothiazolin-3-one) | 150 μg/mL | 115 | 261 μM |
| Antimicrobial agent (NaN$_3$) | 1 mg/mL | 65.9 | 3 mM |
| 80 mM Bis-Tris-HCl buffer, pH 6.5 | 16.7 g/L | 209 | 16 mM |
| 750 mM NaCl | 43.85 g/L | 58.45 | 150 mM |
| Antifoam agent | 400 μg/mL | N/A | 80 μg/mL |

TABLE IV shows a composition for a Bihapten Tracer Reagent suitable for use in this invention.

TABLE IV

| Ingredient | Concentration | Molecular weight (approximate) | Final concentration in reagent |
|---|---|---|---|
| Bihapten tracer | 450 nM | 729 | 90 nM |
| Bovine serum albumin | 36 mg/mL | 68,000 | 106 μM |
| Antimicrobial agent (2-Methyl-4-isothiazolin-3-one) | 150 μg/mL | 115 | 261 μM |
| Antimicrobial agent (NaN$_3$) | 1 mg/mL | 65.9 | 3 mM |

TABLE IV-continued

| Ingredient | Concentration | Molecular weight (approximate) | Final concentration in reagent |
|---|---|---|---|
| 77 mM Tris-HCl buffer, pH 7.4 | 12.1 g/L | 121 | 20 mM |
| 0.9% Triton ® X-100 | 9 mg/mL | 647 | 2.8 mM |
| Antifoam agent | 200 µg/mL | N/A | 40 µg/mL |

EXAMPLE 2

The following example illustrates one embodiment of the assay of this invention a fluorescence polarization immunoassay (FPIA) format.

Bihapten tracer (FK778 coupled to a fluorescein derivative) was diluted to a concentration of 2000 nM in IMx® FPIA line diluent (100 mM Phosphate Buffer, pH 7.5, 0.01% bovine gamma globulin, 0.1% sodium azide) to form the tracer reagent. Monoclonal antibody to FK778 was diluted to a concentration of 100 µg/mL in IMx® FPIA line diluent to form the antibody reagent. A third reagent, Lithium Dodecyl Sulfate (LDS) pretreatment reagent, was prepared by diluting 2% LDS into 100 mM Tris Buffer, pH 7.5, for a final concentration of 0.05% LDS. The LDS pretreatment reagent was used to release any FK778 or bihapten tracer bound to serum albumin in the sample. Calibrators and controls were prepared in a synthetic matrix and ranged in concentration from 0 to 250 µg/mL FK778.

A predilution step for the sample was performed in the IMx® instrument by aspirating and dispensing sample (20 µL) and IMx® FPIA line diluent (780 µL) into the predilution well of a sample cup, followed by incubation for 30 seconds. LDS (75 µL), IMx® FPIA line diluent (905 µL), and sample (20 µL) (i.e., calibrator, control, or specimen) were aspirated and dispensed into an IMx® cuvette. The resulting solution was incubated for 5 minutes, followed by a blank read. Bihapten tracer (75 µL, 2000 nM), monoclonal antibody to FK778 (75 µL), sample (20 µL), and IMx® FPIA line diluent (830 µL) were aspirated and dispensed into the original cuvette. The resulting solution was incubated for 5 minutes, after which a second read was performed. TABLE V shows the values for a calibration curve. FIG. 2 is an example of a dose response curve for FK778 suitable for use in a fluorescence polarization immunoassay.

TABLE V

| Calibrator | [FK778] (µg/mL) | AvgP |
|---|---|---|
| A | 0 | 192.04 |
| B | 10 | 168.98 |
| C | 25 | 145.63 |
| D | 60 | 119.17 |
| E | 125 | 100.09 |
| F | 250 | 86.24 |
| A-F span | | 105.80 |
| Cal B/A | | 0.8799 |
| (E-F)/A | | 0.0721 |

EXAMPLE 3

The purpose of this example is to show preparation of antibody-coated microparticles. Microparticles coated with antibody were prepared as follows:

Microparticles were washed in bulk. MES buffer (32 mL) was transferred to a centrifuge tube (50 mL) by means of a pipette. Microparticles (8 mL, 5% solids) were added to the MES buffer in the centrifuge tube. The microparticles were separated from the buffer by means of externally applied magnetic force, and liquid was removed. The microparticles were resuspended in MES Buffer (40 mL). The microparticles were magnetized and liquid was removed. The microparticles were resuspended in MES buffer (32 mL, 1.25% solids).

The antibody is treated at low pH prior to addition to the microparticles. Anti-FITC antibody (5.55 mg/mL, 1.441 mL) was diluted with Phosphate Buffered Saline (PBS), pH 7.4 (2.559 mL) for a 2 mg/mL solution. PBS (4.0 mL, pH 1.7) was added to anti-FITC antibody (4.0 mL), the resulting solution (1 mg/mL) was incubated for 5 minutes, and then added to washed microparticles (32.0 mL). Microparticles were incubated with the antibody for 10 minutes, with rotation, at room temperature. The microparticles were magnetized and the liquid removed. The microparticles were resuspended in MES Buffer (40.0 mL).

EDAC (33.1 mg) was dissolved in MES Buffer (1.655 mL) to provide a solution having a concentration of 20 mg/mL. EDAC solution (400 µL) was added to the antibody-coated microparticles (40 mL). The mixture was incubated for 30 minutes, with rotation, at room temperature. The microparticles were separated by magnetization and liquid was removed. The microparticles were washed with a mixture of Bovine Serum Albumin/Tween® 20/Tris Buffer (40 mL). The microparticles were resuspended in a mixture of Bovine Serum Albumin/Tween® 20/Tris Buffer (40 mL) and incubated at room temperature for 10 minutes, with rotation, in order to prevent the microparticles from settling. The microparticles were separated by magnetic force and liquid was removed. The microparticles were resuspended in Microparticle Diluent (40 mL). The Microparticle Diluent comprises the ingredients of the Magnetic Microparticle Reagent shown in TABLE I, not including the microparticles. The microparticles were magnetized and liquid removed. The microparticles were resuspended in Microparticle Diluent (40 mL) and stored under refrigeration (1% solids).

Figure 3:
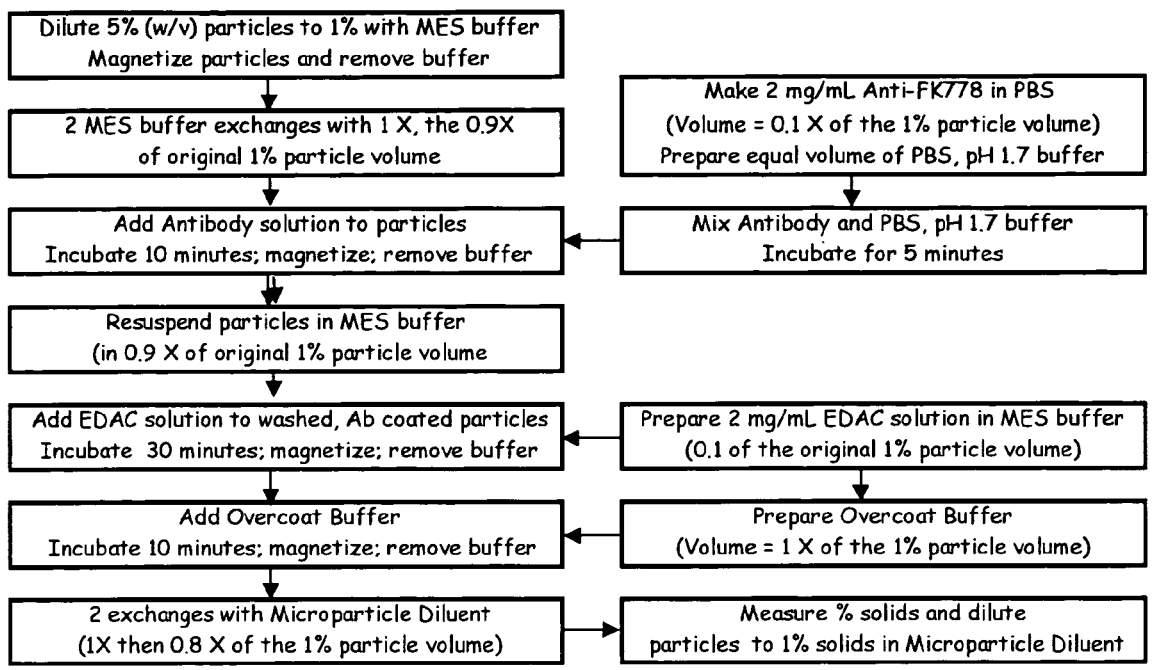
FIG. 3 is a flow chart illustrating a process for coating microparticles.

Prior to use, the microparticles were diluted from 1% to 0.1% solids using microparticle diluent. FIG. 3 is a flow chart illustrating a process for coating microparticles.

EXAMPLE 4

This example describes preparation of conjugates comprising the antibody conjugated to an acridinium label. FIG. 4 illustrates a procedure for preparing conjugates suitable for use in the assay of this invention.

An antibody to FK778 is concentrated to a concentration greater than 7.2 mg/mL, if necessary. CPSP active ester (4 mg/mL) was prepared in DMF. Conjugation buffer was prepared. A reaction mixture (3 mL) containing antibody to FK778 (20 mg), conjugation buffer (200 µL), CPSP active ester (24 µg; 6 µL of 4 mg/mL ester), and PBS was prepared. The mixture was allowed to react for 20 minutes at room temperature. After the reaction, the resulting product was transferred to a dialysis device (Slide-a-lyzer), where it was dialyzed at 4° C. for at least 24 hours against 250 mL dialysis buffer. The dialyzed reaction mixture was filtered through a 0.2 micron filter. The absorbance in a 1 cm cuvette was measured at 370 nm. The absorbance in a 1 cm cuvette was also measured at 280 nm. The acridinium incorporation ratio was calculated, the target being 0.25. Size exclusion HPLC was used to measure aggregates and free CPSP. The conjugate was diluted to a concentration of 300 µg/mL in conjugate diluent (1000×).

The ARCHITECT® instrument measures the assay signal in relative light units (RLU). In the FK778 assay, Calibrator F has concentration of FK778 of 250 µg/mL. Calibrator A contains no analyte.

The shape of the dose response curve was optimized such that both low and high concentrations of FK778 could be measured with good precision and accuracy. Extremely low concentrations of FK778 (<10 µg/mL) are not clinically relevant, but concentrations in the range of about 50 to about 150 µg/mL are therapeutically effective. Varying concentrations of the FK778 analyte, the FK778-fluorescein bihapten tracer, and the conjugate gave an optimal curve shape.

EXAMPLE 5

The purpose of this example is to demonstrate on-board reagent stability for an assay for FK778 designed for the ARCHITECT® instrument.

A small, time-dependent increase in assay signal (decrease in FK778 concentration) during 30-day on-board reagent storage can be observed when the concentration of antifoam agent (Antifoam 10% active, Cat. No. AF9020, GE Silicones, Waterford, N.Y. 12188) is not optimal. Previous studies showed that drift can be reduced by increasing the concentration of antifoam agent in the microparticle reagent. Reagents having increased concentrations of antifoam agent were tested to further reduce drift, as described below. Onboard stability testing was carried out with reagents pre-exposed to a room temperature shaking test (60 minutes), designed to simulate shipping stress. Drift was calculated as the mean Control value from days 31-33 minus the mean Control value for Days 1-5. TABLE VI shows percent drift as a function of concentration of antifoam agent.

TABLE VI

% Control drift during 33 days on board as a function of concentration of antifoam agent

| | Concentration of antifoam agent (ppm) | | |
|---|---|---|---|
| | 200 | 300 | 400 |
| Instrument 1 | | | |
| Low Control (20 µg/mL) | 20.1 | −12.3 | −8.5 |
| Medium Control (75 µg/mL) | −5.9 | −6.2 | −5.4 |
| High Control (150 µg/mL) | −6.8 | −6.5 | −4.2 |
| Instrument 2 | | | |
| Low Control (20 µg/mL) | 20.1 | −6.1 | −6.8 |
| Medium Control (75 µg/mL) | −10.8 | −5.7 | −4.4 |
| High Control (150 µg/mL) | −10.2 | −4.8 | −2.8 |

An additional 30-day on-board stability test was performed at a concentration of antifoam agent of 400 ppm on Instrument 2, the results of which showed minimal drift. Total Precision (including drift) was well below the upper % CV limit of 10%. TABLE VII shows the precision and drift results of a 30-day precision study conducted with reagents stored on board the ARCHITECT® instrument.

TABLE VII

| Instrument 2 | Mean (µg/mL) | % CV | % Drift |
|---|---|---|---|
| Low Control (20 µg/mL) | 20.1 | 3.7% | −1.8% |
| Medium Control (75 µg/mL) | 73.6 | 2.0% | −2.4% |
| High Control (150 µg/mL) | 148.3 | 1.5% | −0.6% |

Figure 5:
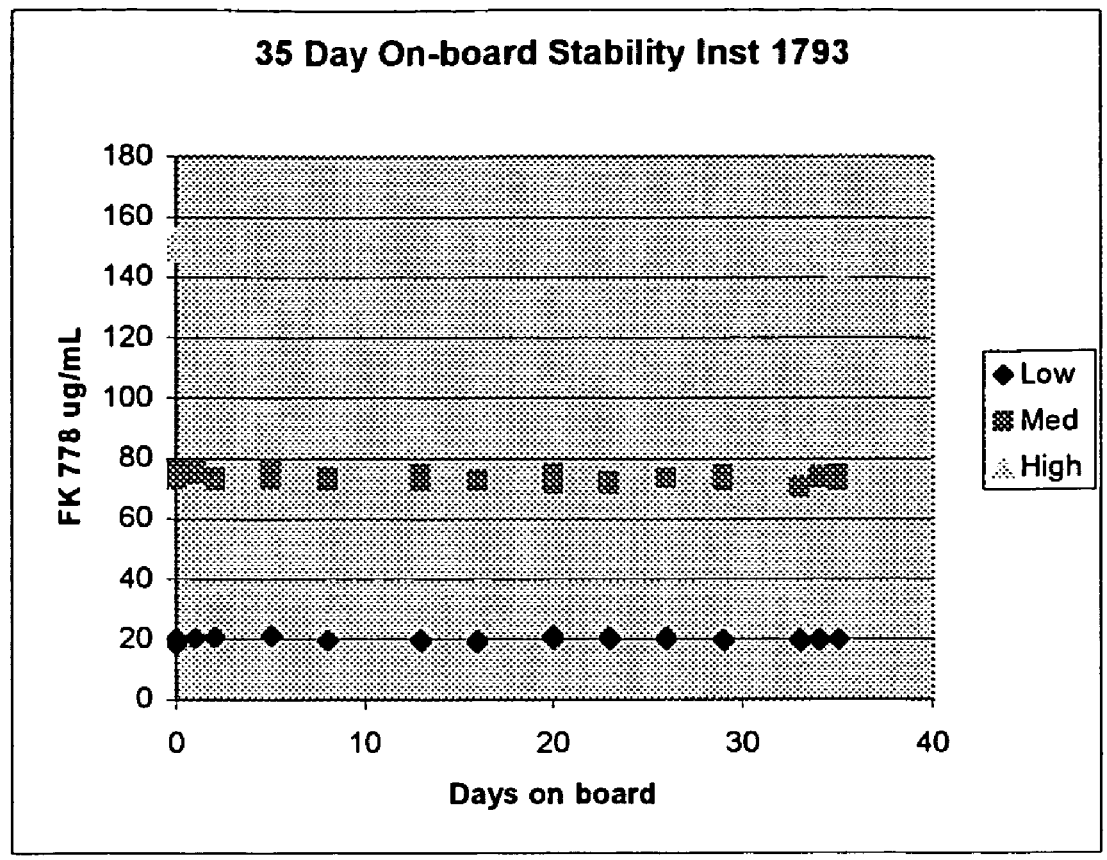
FIG. 5 is a graph illustrating stability of solutions containing FK778 measured over time when these solutions are stored on-board an ARCHITECT® instrument.

FIG. 5 shows the concentration of FK778 as a function of days on board the instrument.

EXAMPLE 6

This example shows the results of a Precision Test. Three lots of FK778 reagents were tested on three ARCHITECT® instruments over a period of 38 days (20 test points) in order to assess precision for both assay controls (synthetic matrix) and on serum spiked with drug. The results summarized below show that both controls and sera in the range 20-200 µg/mL have total % CV below 5%.

Calibration was carried out on day 0 and day 15. Three lots of reagent were used per instrument. Two runs were carried out each day for 20 days over a 38-day period. Duplicate controls and serum panels were used per run. N=720. The results summarized below in TABLES VIII and IX show that both controls and sera in the range 20-200 µg/mL have total % CV below 5%.

TABLE VIII

| Control | Mean (µg/mL) | Standard deviation | Total % CV |
|---|---|---|---|
| Low | 20.9 | 0.9 | 4.2 |
| Medium | 74.5 | 2.3 | 3.1 |
| High | 150.0 | 4.5 | 3.0 |

TABLE IX

| Control | Mean (µg/mL) | Standard deviation | Total % CV |
|---|---|---|---|
| Low | 20.0 | 0.9 | 4.4 |
| Medium | 102.4 | 3.2 | 3.2 |
| High | 209.1 | 6.7 | 3.2 |

EXAMPLE 7

The purpose of this example is to demonstrate correlation of assay results for concentration of FK778 determined by an ARCHITECT® instrument with assay results for concentration of FK778 determined by liquid chromatography/tandem mass spectrometry (hereinafter LC/MS/MS). Pools of frozen liver transplant specimens previously tested by an external LC/MS/MS method were retested on an ARCHITECT® instrument and compared to LC/MS/MS results generated by an internal method, optimized to match the outside method. The LC/MS/MS method used independently prepared calibrators.

TABLE X

| Pool no. | N = 1 LC/MS/MS | N = 2 ARCHITECT ® |
|---|---|---|
| 1 | 97.1 | 99.9 |
| | | 96.7 |

TABLE X-continued

| Pool no. | N = 1 LC/MS/MS | N = 2 ARCHITECT ® |
|---|---|---|
| 2 | 13.16 | 12.6 |
|   |   | 13.2 |
| 3 | 27.76 | 29.9 |
|   |   | 28.4 |
| 4 | 31.69 | 33.7 |
|   |   | 32.7 |
| 5 | 92.83 | 91.9 |
|   |   | 94.1 |
| 6 | 42.15 | 44.9 |
|   |   | 45.0 |
| 7 | 56.39 | 56.1 |
|   |   | 56.0 |
| 8 | 73.86 | 75.0 |
|   |   | 74.1 |
| 9 | 130.46 | 133.3 |
|   |   | 135.1 |
| 10 | 135.25 | 144.2 |
|   |   | 142.5 |
| 11 | 42.47 | 43.7 |
|   |   | 44.4 |
| 12 | 103.72 | 103.5 |
|   |   | 107.0 |

The results show that excellent correlation can be obtained with the reference method, even when independently prepared calibrators are used.

EXAMPLE 8

This example illustrates lack of interference by Rheumatoid Factor (RF) in the assay for FK778 on an ARCHITECT® instrument. Clinical specimens with elevated levels of RF (antibodies to the Fc portion of IgG) were tested for interference in the assay employing the ARCHITECT® instrument. Specimens were tested with and without drug present. The results shown in TABLE XI indicate that there was no interference when samples were tested without drug. There was some variability of greater than 10% in drug recovery with these samples, but the average recovery was 102%, and there was no strong bias that correlates to RF levels.

TABLE XI

| Sample ID | [RF] (IU/mL) | [Specimen Alone] (µg/mL) FK778 | [Specimen + Spike] (µg/mL) FK778 | [Specimen + Matrix] (µg/mL) FK778 | Spiked % Recovery |
|---|---|---|---|---|---|
| 327 | 335 | 0.64 | 90.64 | 0.49 | 113% |
| 347 | 118 | 0.8 | 99.78 | 0.68 | 125% |
| 356 | 105 | 0.76 | 74.92 | 0.75 | 94% |
| 357 | 212 | 0.68 | 78.18 | 0.75 | 98% |
| 358 | 392 | 0.89 | 83.45 | 0.71 | 104% |
| 364 | 158 | 0.76 | 80.93 | 0.9 | 101% |
| 369 | 93 | 0.77 | 70.21 | 1.31 | 88% |
| 372 | 118 | 0.14 | 77.29 | 1.03 | 97% |
| 407 | 188 | 0.28 | 82.07 | 0.55 | 102% |
| 413 | 87 | 0.91 | 80.67 | 1.13 | 101% |
| Cal A spike | | | 80.07 | 0.7 | |

EXAMPLE 9

This example illustrates the effect of human anti-mouse antibody (HAMA) interference. Purified human anti-mouse antibody (HAMA) at a concentration of 1 mg/mL was tested as a sample in the assay and was read as 0.26 µg/mL, which was well below the limit of detection of approximately 1.5 µg/mL. This result confirmed that the Mouse IgG present in the reagents blocked the effect of HAMA.

EXAMPLE 10

This example illustrates interference with prescription drugs. Interference was tested for 44 of 45 prescription drugs at levels recommended in NCCLS document EP-7P. Interference was tested in the presence of FK778 and absence of FK778 in the sample. Interference was defined as greater than 5 µg/mL (without FK778) or greater than 10% (with FK778). Interference was observed only with fluorescein and A77, 1726 (the active metabolite of Leflunomide). Both interferences were expected; fluorescein because of its competition with the FK778-fluorescein bihapten tracer and A77, 1726 because of its similarity in structure to FK778. TABLE XII shows the results of interference testing.

TABLE XII

| Drug Tested | [Drug] (µg/mL) | [Neg Control] (µg/mL) | [Neg Control + Drug] (µg/mL) | [Pos Control] (µg/mL) | [Pos Control + Drug] (µg/mL) | % Interference |
|---|---|---|---|---|---|---|
| 4-Aminosalicylic Acid | 800 | 0.2 | 0.5 | 70.0 | 73.6 | 5.2% |
| 5-Fluorocytosine | 301 | 0.2 | 0.1 | 71.7 | 70.8 | −1.2% |
| 5-Fluorouracil | 400 | 0.4 | 0.6 | 74.8 | 73.8 | −1.4% |
| Acetaminophen | 25 | 0.4 | 0.5 | 71.3 | 71.9 | 0.9% |
| Acetylsalicylic Acid | 600 | 0.6 | 0.6 | 70.7 | 69.4 | −1.9% |
| Amphotericin B | 105 | 0.3 | 0.1 | 70.5 | 70.7 | 0.2% |
| Azathioprine | 300 | 0.5 | 0.3 | 70.0 | 70.7 | 0.9% |
| Caffeine | 60 | 0.0 | 0.0 | 71.4 | 71.0 | −0.6% |
| Cefazolin | 1259 | 0.0 | 0.6 | 69.3 | 68.8 | −0.7% |
| Cefotaxime | 320 | 0.3 | 0.3 | 72.3 | 71.7 | −0.8% |
| Cefoxitin | 705 | 0.3 | 0.2 | 72.3 | 72.7 | 0.5% |
| Ceftriaxone | 733 | 0.3 | 0.1 | 73.1 | 72.6 | −0.7% |
| Cefuroxime | 632 | 0.2 | 0.4 | 72.8 | 72.2 | −0.8% |
| Cephalexin | 117 | 0.5 | 0.1 | 71.6 | 72.9 | 1.8% |
| Cyclophosphamide | 401 | 0.3 | 0.6 | 72.3 | 72.7 | 0.7% |
| Cyclosporine | 5 | 0.0 | 0.2 | 71.3 | 70.5 | −1.1% |
| Ethosuximide | 250 | 0.1 | 0.4 | 70.5 | 70.8 | 0.4% |
| Fenoprofen | 421 | 0.8 | 0.2 | 54.0 | 53.0 | −1.8% |

TABLE XII-continued

| Drug Tested | [Drug] (μg/mL) | [Neg Control] (μg/mL) | [Neg Control + Drug] (μg/mL) | [Pos Control] (μg/mL) | [Pos Control + Drug] (μg/mL) | % Interference |
|---|---|---|---|---|---|---|
| Fluorescein (High Conc.) | 400 | 0.3 | 7.8* | 42.5 | 89.6 | 111%** |
| A77,1726 (Leflunomide Derivative) | 200 | 0.5 | 94.9* | 70.5 | 146.7 | 108%** |
| Furosemide | 60 | 0.3 | 0.5 | 71.5 | 71.5 | 0.0% |
| Gabapentin | 90 | 0.3 | 0.3 | 67.9 | 66.2 | −2.5% |
| Gemfibrozil | 75 | 0.4 | 0.8 | 71.3 | 71.8 | 0.8% |
| Guaifenesin | 3013 | 0.3 | 0.1 | 67.4 | 66.9 | −0.8% |
| Ibuprofen | 500 | 0.4 | 0.2 | 54.6 | 53.5 | −2.0% |
| Metformin | 51 | 0.3 | 0.4 | 71.9 | 73.1 | 1.6% |
| Metronidazole | 120 | 0.0 | 0.1 | 70.8 | 70.2 | −0.8% |
| Mycophenolic Acid | 125 | 0.4 | 0.5 | 72.9 | 72.0 | −1.2% |
| Nabumetone | 316 | 0.4 | 0.3 | 70.1 | 71.5 | 2.1% |
| N-acetyl cysteine | 2709 | 0.2 | 0.5 | 52.5 | 52.4 | −0.2% |
| Naproxen | 500 | 0.1 | 0.5 | 71.7 | 71.7 | 0.0% |
| Niacin | 40 | 0.4 | 0.5 | 74.8 | 73.1 | −2.3% |
| Nifedipine | 400 | 0.4 | 0.4 | 74.7 | 74.5 | −0.2% |
| Phenobarbital | 100 | 0.8 | 1.0 | 58.5 | 59.3 | 1.4% |
| Prednisone | 0.3 | 0.2 | 0.2 | 70.6 | 70.2 | −0.6% |
| Probenecid | 600 | 0.0 | 0.1 | 70.9 | 71.6 | 1.1% |
| Salicylic Acid | 599 | 0.1 | 0.2 | 70.5 | 70.0 | −0.8% |
| Sirolimus | 0.1 | 0.6 | 0.6 | 72.7 | 72.1 | −0.7% |
| Sodium Diatrizoate | 200 | 0.3 | 0.4 | 71.9 | 71.7 | −0.3% |
| Sulfadiazine | 272 | 0.2 | 0.4 | 71.5 | 72.0 | 0.7% |
| Sulfamethoxazole | 400 | 0.4 | 0.5 | 72.8 | 73.6 | 1.1% |
| Sulfisoxazole | 300 | 0.6 | 0.4 | 72.6 | 72.4 | −0.3% |
| Tacrolimus | 0.1 | 0.0 | 0.3 | 71.3 | 72.0 | 1.0% |
| Trimethoprim | 40 | 0.0 | 0.0 | 71.4 | 69.4 | −2.8% |
| Valproic Acid | 500 | 0.3 | 0.0 | 71.5 | 71.1 | −0.6% |

*Interferes > 5 μg/mL
**Interferes > 10%

Fluorescein is used in in vivo diagnostic procedures to measure blood flow in the eye and is not expected to be present in patients undergoing a transplant. Nevertheless, fluorescein was tested more thoroughly to estimate the magnitude of the interference at concentrations lower than 400 μg/mL. The data obtained, which is shown in TABLE XIII, indicates that interference drops below 10% in the range of 30 to 50 μg/mL.

TABLE XIII

| | Fluorescein measured as FK778 | | | % Fluorescein interference | | |
|---|---|---|---|---|---|---|
| [Fluorescein] μg/mL | Low FK778 (~20 μg/mL) | Med FK778 (~70 μg/mL) | High FK778 (~125 μg/mL) | Low FK778 | Med FK778 | High FK778 |
| 400 | 44.04 | 129.72 | 220.8 | 118% | 100% | 101% |
| 0 | 20.16 | 64.74 | 109.95 | | | |
| 200 | 33.42 | 103.68 | 190.11 | 69% | 53% | 51% |
| 0 | 19.75 | 67.62 | 125.95 | | | |
| 100 | 27.8 | 87.86 | 168.83 | 38% | 28% | 26% |
| 0 | 20.2 | 68.67 | 134.19 | | | |
| 50 | 24.58 | 79.98 | 161.46 | 19% | 9% | 14% |
| 0 | 20.61 | 73.58 | 141.94 | | | |
| 30 | | 72.54 | | | 8% | |
| 0 | | 67.46 | | | | |

Additional testing was also carried out with A77, 1726 to assess the cross-reactivity of this molecule in the presence and absence of FK778. The results in TABLE XIV show that the percent cross-reactivity varied from a high of 47% to a low of 13% in the presence of a large amount of competing FK778.

TABLE XIV

| [A77,1726] μg/mL | A77,1726 measured as FK778 | | | | % Cross-reactivity A77,1726 | | | |
|---|---|---|---|---|---|---|---|---|
| | Zero FK778 | Low FK778 | Med FK778 | High FK778 | Zero FK778 | Low FK778 | Med FK778 | High FK778 |
| 200 | 94.9 | 104.6 | 145.5 | 209.3 | 47% | 42% | 37% | 34% |
| 0 | 0.5 | 20.8 | 70.6 | 140.4 | | | | |
| 100 | | 62.6 | 103.4 | 170.1 | | 42% | 31% | 23% |
| 0 | | 20.8 | 72 | 147.4 | | | | |
| 50 | | 42.3 | 85 | 152.9 | | 43% | 24% | 13% |
| 0 | | 20.8 | 73.1 | 146.6 | | | | |

EXAMPLE 11

The purpose of this example is to testing FK778 metabolites M1 and M3 for interference. The FK778 metabolites were tested as interfering substances in the absence of FK778, as shown in TABLE XV. As expected from the specificity of the antibody to FK778, cross-reactivity is not measurable for M1 and is approximately only 1% for M3. The structures of M1 and M3 are shown below.

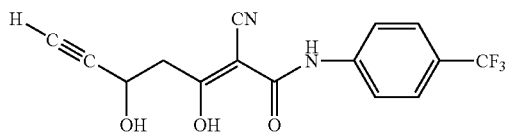

FK778 Metabolite M3

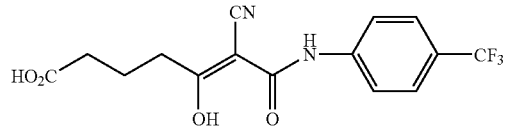

FK 778 Metabolite M1

TABLE XV

| Metabolite | Concentration (μg/mL) | Measured FK778 (μg/mL) | % Cross-reactivity |
|---|---|---|---|
| M1 | 1033 | Less than 1.5 | Less than limit of detection |
| M3 | 1129 | 8.6 | 0.8% |
| M3 | 1129 | 7.8 | 0.7% |
| M3 | 565 | 5.6 | 1.0% |
| M3 | 565 | 3.8 | 0.7% |
| M3 | 226 | 3.4 | 1.5% |
| M3 | 226 | 2.8 | 1.2% |
| M3 | 57 | Less than 1.5 | Less than limit of detection |

EXAMPLE 12

This example illustrates the effect of heat stress and freeze-thaw on the reagents for the FK778 assay. Reagents were stored frozen at 4° C., 22° C., 30° C., and 45° C. for five days and tested for ability to retain an acceptable calibration curve. Data is set forth in TABLE XVI. The only significant shift in RLU signal was seen at 45° C. (RLU decrease in Cal A to Cal C and RLU increase in Cal E and Cal F). Nevertheless, the reagents stressed at 45° C. retained acceptable curve shape. The measured data are in RLU.

TABLE XVI

| | [FK778] (μg/mL) | Storage conditions for five days | | | | |
|---|---|---|---|---|---|---|
| | | 2-8° C. | 22° C. | 30° C. | 45° C. | −20° C. |
| CAL A | 0 | 1,015,528 | 1,015,072 | 1,022,517 | 941,309 | 1,003,045 |
| CAL B | 10 | 801,450 | 799,379 | 807,393 | 757,486 | 795,841 |
| CAL C | 25 | 615,720 | 613,335 | 624,129 | 599,162 | 600,028 |
| CAL D | 60 | 419,994 | 410,027 | 419,843 | 412,640 | 407,553 |
| CAL E | 125 | 261,045 | 259,427 | 262,146 | 264,602 | 256,081 |
| CAL F | 250 | 155,309 | 154,695 | 155,664 | 159,831 | 154,725 |
| | Specification | | | | | |
| B/A | 0.72-0.82 | 0.789 | 0.788 | 0.790 | 0.805 | 0.793 |
| E-F/A | 0.08-0.12 | 0.104 | 0.103 | 0.104 | 0.111 | 0.101 |
| | RLU Shift from 2-8° C. Control | | | | | |
| CAL A | 0 | 0.0% | 0.0% | 0.7% | −7.3% | −1.2% |
| CAL B | 10 | 0.0% | −0.3% | 0.7% | −5.5% | −0.7% |
| CAL C | 25 | 0.0% | −0.4% | 1.4% | −2.7% | −2.5% |
| CAL D | 60 | 0.0% | −2.4% | 0.0% | −1.8% | −3.0% |
| CAL E | 125 | 0.0% | −0.6% | 0.4% | 1.4% | −1.9% |
| CAL F | 250 | 0.0% | −0.4% | 0.2% | 2.9% | −0.4% |

EXAMPLE 13

This example illustrates stability of reagents used in the assay for FK778 to microbial challenge. Compositions containing FK778 were spiked with a standard microorganism panel used to determine the effectiveness of the antimicrobial agents in the compositions and to test the effect of microorganisms on assay performance. For testing of antimicrobial effectiveness, samples were stored at room temperature and tested for microbial count at 14 and 28 days. Spiked compositions were also incubated 37 days at temperatures ranging from 2 to 8° C. and then assayed (Calibrators and Controls in replicates of 21). The data in TABLES XVII, XVIII, XIX, XX indicate that these microorganisms are killed by the antimicrobial agents and do not cause any performance failures. The data in TABLES XVII and XVIII show microbial count. The data in TABLES XIX, XX, and XXI show signal in RLU.

TABLE XVII

| Day | Group I Candida albicans | Group II Aspergillus Niger | Group III E. Coli | Group IV Pseudomonas aeruginosa | Group V Negative Control | Group VI Pseudomonas fluoroscens | Group VII Staphylococcus aureus |
|---|---|---|---|---|---|---|---|
| Innoc | 3.80E+05 | 1.20E+06 | 1.90E+06 | 7.20E+06 | 0 | 5.20E+05 | 1.30E+06 |
| 14 | 0 | 0 | 0 | 0 | 0 | 0 | 0 |
| 28 | 0 | 0 | 0 | 0 | 0 | 0 | 0 |
| Innoc | 3.80E+05 | 1.20E+06 | 1.90E+06 | 7.20E+06 | 0 | 5.20E+05 | 1.30E+06 |
| 14 | 0 | 0 | 0 | 0 | 0 | 0 | 19,000 |
| 28 | 0 | 0 | 0 | 0 | 0 | 0 | 6 |
| Innoc | 3.80E+05 | 1.20E+06 | 1.90E+06 | 7.20E+06 | 0 | 5.20E+05 | 1.30E+06 |
| 14 | 0 | 0 | 0 | 0 | 0 | 0 | 0 |
| 28 | 0 | 0 | 0 | 0 | 0 | 0 | 0 |

TABLE XVIII

| Day | Candida albicans | Aspergillus Niger | E. Coli | Pseudomonas aeruginosa | Negative Control | Pseudomonas fluoroscens | Staphylococcus aureus |
|---|---|---|---|---|---|---|---|
| (Conjugate (Proclin 300) | | | | | | | |
| Innoc | 3.80E+05 | 1.20E+06 | 1.90E+06 | 7.20E+06 | 0 | 5.20E+05 | 1.30E+06 |
| 14 | 0 | 0 | 0 | 0 | 0 | 0 | 0 |
| 28 | 0 | 0 | 0 | 0 | 0 | 0 | 0 |
| Microparticle (Proclin 950 + NaAzide) | | | | | | | |
| Innoc | 3.80E+05 | 1.20E+06 | 1.90E+06 | 7.20E+06 | 0 | 5.20E+05 | 1.30E+06 |
| 14 | 0 | 0 | 0 | 0 | 0 | 0 | 19,000 |
| 28 | 0 | 0 | 0 | 0 | 0 | 0 | 6 |
| Bihapten Tracer (Proclin 950 + Na Azide) | | | | | | | |
| Innoc | 3.80E+05 | 1.20E+06 | 1.90E+06 | 7.20E+06 | 0 | 5.20E+05 | 1.30E+06 |
| 14 | 0 | 0 | 0 | 0 | 0 | 0 | 0 |
| 28 | 0 | 0 | 0 | 0 | 0 | 0 | 0 |

TABLE XIX

| | | Group | | | |
|---|---|---|---|---|---|
| Agent | [FK778] µg/mL | Group I Candida albicans | Group II Aspergillus Niger | Group III E. Coli | Group IV Pseudomonas aeruginosa |
| CAL A | 0 | 1,006,894 | 1,009,214 | 1,005,748 | 1,000,710 |
| CAL B | 10 | 756,737 | 764,359 | 759,495 | 756,648 |
| CAL C | 25 | 558,357 | 560,736 | 557,901 | 557,007 |
| CAL D | 60 | 356,182 | 357,137 | 358,530 | 356,938 |
| CAL E | 125 | 217,183 | 218,367 | 217,212 | 217,696 |
| CAL F | 250 | 127,615 | 128,091 | 128,194 | 127,906 |
| Spec | | | | | |
| B/A | 0.72–0.82 | 0.752 | 0.757 | 0.755 | 0.756 |
| E-F/A | 8-12% | 8.90% | 8.95% | 8.85% | 8.97% |
| Data Summary of 20 replicates of each Calibrator and Control level | | | | | |
| Expected | | | | | |
| Cal B Mean | 10 | 10.0 | 9.9 | 9.9 | 9.9 |
| Cal B % CV | | 4.7 | 4.0 | 4.2 | 3.4 |
| Cal C Mean | 25 | 25.2 | 25.3 | 25.4 | 25.3 |

TABLE XIX-continued

| | | | | |
|---|---|---|---|---|
| Cal C % CV | | 2.6 | 1.9 | 2.9 | 2.3 |
| Cal D Mean | 60 | 59.8 | 59.7 | 59.3 | 59.6 |
| Cal D % CV | | 2.0 | 2.4 | 2.1 | 1.6 |
| Cal E Mean | 125 | 124.7 | 123.9 | 125.1 | 124.5 |
| Cal E % CV | | 1.7 | 2.3 | 2.0 | 2.1 |
| Cal F Mean | 250 | 251.3 | 253.3 | 251.6 | 252.2 |
| Cal F % CV | | 2.5 | 2.0 | 1.6 | 1.7 |
| Low Ctl Mean | 20 | 20.6 | 20.7 | 20.2 | 20.4 |
| Low Ctl % CV | | 3.7 | 3.2 | 3.5 | 3.8 |
| Med Ctl Mean | 75 | 74.5 | 73.1 | 74.8 | 74.2 |
| Med Ctl % CV | | 2.9 | 2.8 | 2.4 | 2.9 |
| High Ctl Mean | 150 | 150.6 | 149.4 | 150.6 | 150.6 |
| High Ctl % CV | | 2.3 | 2.0 | 1.7 | 2.3 |

TABLE XX

| | Group | | | |
|---|---|---|---|---|
| Agent | [FK778] µg/mL | Group V Negative Control | Group VI *Pseudomonas fluoroscens* | Group VII *Staphylococcus aureus* |
| CAL A | 0 | 1,001,377 | 1,004,756 | 1,003,511 |
| CAL B | 10 | 763,399 | 757,117 | 756,423 |
| CAL C | 25 | 564,383 | 559,448 | 557,541 |
| CAL D | 60 | 363,095 | 357,295 | 356,227 |
| CAL E | 125 | 222,968 | 217,352 | 217,012 |
| CAL F | 250 | 130,984 | 128,576 | 127,366 |
| Spec | | | | |
| B/A | 0.72-0.82 | 0.762 | 0.754 | 0.754 |
| E-F/A | 8-12% | 9.19% | 8.84% | 8.93% |
| Expected | | | | |
| Cal B Mean | 10 | 9.9 | 10.0 | 9.9 |
| Cal B % CV | | 4.0 | 5.7 | 6.4 |
| Cal C Mean | 25 | 25.3 | 25.2 | 25.2 |
| Cal C % CV | | 2.0 | 2.3 | 3.4 |
| Cal D Mean | 60 | 59.7 | 59.7 | 59.7 |
| Cal D % CV | | 2.6 | 2.3 | 1.7 |
| Cal E Mean | 125 | 124.0 | 125.1 | 124.6 |
| Cal E % CV | | 2.1 | 2.2 | 2.3 |
| Cal F Mean | 250 | 253.0 | 250.6 | 251.6 |
| Cal F % CV | | 1.6 | 1.6 | 1.6 |
| Low Ctl Mean | 20 | 20.4 | 20.3 | 20.7 |
| Low Ctl % CV | | 2.7 | 2.9 | 3.2 |
| Med Ctl Mean | 75 | 73.9 | 74.4 | 74.8 |
| Med Ctl % CV | | 1.9 | 2.1 | 2.6 |
| High Ctl Mean | 150 | 149.6 | 149.6 | 149.9 |
| High Ctl % CV | | 1.5 | 2.9 | 2.0 |

EXAMPLE 14

The purpose of this example is to demonstrate multi-lot stability. Three independent lots of reagents in their final formulation were stored at reduced temperature to determine their long-term stability. In addition, one lot was tested in the inverted position to determine the effect of long-term contact with the cap liner. Also included in the first month of testing was a shipping stress test on one lot. The results are shown in TABLE XXI. The main effect of long-term storage was expected to be a slow decrease in RLU signal, the measurements of which are reported in TABLE XXI. The stability of the curve shape is measured by the B/A ratio, which is also reported. The shipping stress data shows acceleration of RLU decrease in the Cal A-D region of the curve, but retention of acceptable B/A. The measured data are in RLU.

TABLE XXI

Calibration Curve Signal - Temperature stress and 6 month stability study

| | Test Lot | | | | | | | | % Change in Raw Signal | | | | |
|---|---|---|---|---|---|---|---|---|---|---|---|---|---|
| | Lot 1 | Lot 2 | Lot 3 | Lot 2 Stress | Lot 1 | Lot 2 | Lot 2 | Lot 3 | | | | | |
| | None | None | None | Temp Stress | 2-8° C. | Inverted | 2-8° C. | 2-8° C. | Day 14 | Day 182 | Day 182 | Day 182 | Day 182 |
| | Test day | | | | | | | | | | | | |
| | Day 0 | Day 0 | Day 0 | Day 14 | Day 182 | Day 182 | Day 182 | Day 182 | | | | | |
| CAL A | 1,264,732 | 1,260,372 | 1,168,686 | 1,208,971 | 1,260,431 | 1,263,332 | 1,244,019 | 1,180,200 | -4% | 0% | 0% | -1% | 1% |
| CAL B | 982,786 | 974,035 | 922,384 | 946,794 | 966,752 | 961,420 | 961,171 | 915,368 | -3% | -2% | -1% | -1% | -1% |
| CAL C | 728,684 | 719,546 | 687,400 | 701,828 | 708,587 | 703,389 | 689,781 | 674,169 | -2% | -3% | -2% | -4% | -2% |
| CAL D | 475,288 | 463,661 | 439,889 | 456,092 | 452,446 | 443,983 | 439,546 | 428,498 | -2% | -5% | -4% | -5% | -3% |
| CAL E | 293,564 | 284,344 | 270,038 | 288,531 | 281,067 | 275,184 | 268,682 | 265,225 | 1% | -4% | -3% | -6% | -2% |
| CAL F | 174,994 | 170,908 | 159,212 | 173,599 | 168,113 | 164,130 | 158,859 | 154,522 | 2% | -4% | -4% | -7% | -3% |
| B/A Ratio 0.72-0.82 | 0.78 | 0.77 | 0.79 | 0.78 | 0.77 | 0.76 | 0.77 | 0.78 | | | | | |

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for determining the amount of FK778 in a test sample comprising the steps of:
   (a) incubating a mixture comprising a test sample suspected of containing FK778, a solid phase coupled to an antibody specific for a first hapten, a bihapten comprising FK778 or an analogue of FK778 and the first hapten, and a reagent mixture comprising an antibody to FK778 conjugated to a label and an antibody to FK778 not conjugated to a label, wherein the ratio of the antibody to FK778 conjugated to a label to the antibody to FK778 not conjugated to a label in the reagent mixture ranges from about 1:135 to about 1:225, to form a detectable complex comprising (i) the antibody to FK778 conjugated to the label, (ii) a bihapten comprising a first hapten and FK778 or an analogue of FK778, and (iii) the solid phase coupled to the antibody specific for the first hapten;
   (b) separating the solid phase from the mixture;
   (c) measuring the amount of label bound to the solid phase; and
   (d) determining the amount of FK778 in the test sample from the amount of label measured.

2. The method of claim 1, wherein the label is a chemiluminescent label.

3. The method of claim 2, wherein said label is an acridinium label.

* * * * *